United States Patent [19]

McCarthy et al.

[11] 4,361,436
[45] Nov. 30, 1982

[54] COMPOSITION FOR PLANT GROWTH REGULATION

[75] Inventors: Robert F. McCarthy, Redbank; Jonathan M. Kliegman, Wayne, both of N.J.

[73] Assignee: GAF Corporation, New York, N.Y.

[21] Appl. No.: 163,441

[22] Filed: Jun. 26, 1980

Related U.S. Application Data

[63] Continuation-in-part of Ser. No. 833,757, Sep. 16, 1977, abandoned.

[51] Int. Cl.$^3$ ............................................. A01N 57/12
[52] U.S. Cl. .......................................... 71/86; 71/94; 71/95
[58] Field of Search ................................ 71/86, 95, 94

[56] References Cited

U.S. PATENT DOCUMENTS 3,879,188  2/1975  Fritz et al. ............................ 71/86
4,191,555  3/1980  Kliegman ............................. 71/95

FOREIGN PATENT DOCUMENTS 369889  2/1973  U.S.S.R. .

OTHER PUBLICATIONS

S. African Pat. 690539B, Chem. Abst. vol. 75 (1971) 109261k.
Collective Index, vol. 76-85, (1972-1976), Chem. Abst., p. 34553.
Belg. Pat. 657536-Chem. Abst., vol. 64, (1966) 13321d.

Primary Examiner—Catherine L. Mills
Attorney, Agent, or Firm—James Magee, Jr.; Marilyn J. Maue

[57] ABSTRACT

A composition comprising a mixture of a N-heterocyclic monoamide such as e.g. N-methyl pyrrolidone or a polymer thereof, and a 2-halo-ethylphosphonic acid useful for the treatment of plants including trees, shrubs, field crops, grasses and ornamentals to achieve enhanced plant growth regulatory effects. Of particular interest are the treatments of apple trees to promote fruit redening; treatment of cherry, hazel and walnut trees to advance fruit loosening; treatment of cucumbers to induce stunting and to promote female sex expression; treatment of tobacco to hasten maturation and to inhibit tillering and treatment of cotton plants prior to harvesting to provide defoliation synchronized with increased, boll opening in preparation for harvest of quality cotton in high yields.

19 Claims, No Drawings

COMPOSITION FOR PLANT GROWTH REGULATION

This application is a continuation-in-part of U.S. application Ser. No. 833,757, filed Sept. 16, 1977, now abandoned.

In one aspect the present invention relates to an improved composition for plant growth regulation and inducing hormonal ethylene plant responses, such as those disclosed in ETHYLENE IN PLANT BIOLOGY by Frederick B. Abeles, Academic Press Inc., New York, 1973 (ISBN 0-12-041450-3), pages 1 through 272 and in BIOCHEMISTRY AND PHYSIOLOGY OF PLANT GROWTH SUBSTANCES (Proceedings of the 6th International Conference on Plant Growth Substances, July 24–29, 1967), edited by F. Wightman and G. Setterfield, The Runge Press, Ltd., Ottowa Canada 1968, pages 1217 through 1316 and 1393 through 1399.

In a second and more particular aspect, the present invention is directed to the plants of the genus Gossypium which include the commercially grown varieties *Gossypium arboreum*, a perennial tree variety; *Gossypium hissupum*, a multibranched shrub and *Gossypium barbadense*, a shrub having unusually long white lustrous fibers of which pima cotton is an example and other varieties. Generally, the development of a cotton crop starts with the formation of a flower bud or square which subsequently matures into a cotton boll. Upon ripening the boll splits open exposing a mass of long white seed hairs (lint) and shorter hairs (fuzz) covering the seeds contained in a 3-5 valve boll capsule. This breaking of the boll, or dehiscence, presents the cotton fiber for harvest by collection with spindle-like pickers which pull the cotton from the open bolls or with strippers which collect the entire boll.

Usually, the lapse of time from square set to boll break varies over a relatively long period, e.g., from about 40 to 70 days; although, the lapse of time from square set to the development of mature cotton fiber inside the unopened boll is only from about 30 to 50 days. Because of the extensive variation in time for dehiscence, it has been necessary to collect the cotton in more than one harvesting operation; however, due to climatic conditions and increased exposure to infestation, a poorer quality cotton is usually recovered from the second harvest.

Much research has been directed to shortening the growing season of cotton by opening the bolls prematurely. It has also been an aim of research to develop a treatment forcing early maturity of the bolls. However, these treatments have generally resulted in a small, light stapled crop, i.e., shorter and fewer seed hairs with increased fuzz.

A second important consideration in the harvesting of cotton is defoliation. Selective and substantially complete abscission of leaves and petioles before harvesting is needed to make the bolls available to the pickers and to avoid collection of unwanted debris which stains cotton fibers and leads to subsequent separation problems and breaking of fibers. Many defoliants are commercially available and have been employed for this purpose, but such chemicals generally do not promote any plant response other than defoliation. It is also desirable to avoid excessively rapid defoliation before maturing bolls have opened or are fully developed, since excessive leaf drop interrupts transpiration and puts undue stress on the plant, interrupting continuance of normal plant processes. Further, the developing bolls are robbed of nourishment by the absence of leaves and the tendency of the plant system to direct growth effect in the development of new leaves to compensate for those lost, in preference to continued boll development. These effects contribute to poor fiber stable and underdeveloped bolls.

The commercial value of a cotton crop is primarily based on the quality of the fiber. Staple length is of prime importance, that is to say, the longer and more uniform the fibers, the more valuable the crop. Other considerations including color, strength and elongation are also important in judging quality. Accordingly, it is highly desirable that the cotton be harvested as soon as possible after dehiscence so that all occasion of staining caused by rainfall or contact with foliar debris be substantially eliminated. Since boll dehiscence induced by chemicals and chemically induced defoliation proceed at different rates, and further, since the defoliants show substantially no effect on dehiscence and vice versa it has been necessary to employ several separate sprays to the standing crop at staged intervals prior to harvesting. Obviously, this practice has significantly increased the cost of cotton production.

Recently chloroethylphosphoic acid has been proposed as a defoliant for cotton; however, the dosages required for significant defoliation, e.g., more than 35% leaf drop, is reported to be in the range of 20,000-50,000 ppm acid (see U.S. Pat. No. 3,879,188). At these concentration levels it has been found that abscission is nonselective and that bolls, as well as leaves, are dropped as a result of the treatment. In a paper presented at the Beltwide Cotton Research Conference, January 1968, by Page W. Morgan, and subsequently published in Plant Physiology 44(3), 337–341, 1969, it is reported that certain cotton plants treated with only 2,000 ppm chloroethylphosphonic acid resulted in comparatively rapid abscission of squares, flowers, and immature bolls. Obviously the cotton from abscissed bolls is not recovered and represents a loss in yield.

Insofar as an induced ripening effect of chemicals is concerned, D. S. Kittock et al., Journal Environ, Qual. 1973, 2(3), 405–8; and C. L. Hsu et al., Pysiol. Plant, 1976, 36(2) 150-3 report that several deleterious side-effects result from forced maturation of certain cotton crops, particularly that ethephon has been found to have an inhibiting effect on normal fiber development.

Another disadvantage of chemicals which induce ripening is that, although the growing season of the crop can be somewhat shortened, the need for multiple harvesting is not eliminated since the ripening effect is indiscriminate and merely advances all stages of development at the same rate. Accordingly, what is needed is a chemical or composition which can regulate growth by selectively defoliating leaves and petioles after having advanced the ripening of immature bolls within a shorter time than normally obtained, and preferentially at a faster rate than that of mature bolls so as to standardize the time of boll break, thus eliminating the need for multiple harvesting, and to synchronize precedence of dehiscence over defoliation so as to obviate the need for multiple applications of different chemicals.

It is an object of this invention to accomplish the above and other advantages in the treatment of cotton corps prior to harvest.

Another object of the invention is to provide an improved plant growth regulating composition having various desirable effects, such as inducing promotional and inhibitory growth responses in a plant.

Another object of this invention is to provide a single multi-purpose composition for the treatment of cotton.

Another object is to provide a composition for ripening plant parts.

Another object is to provide a composition for increasing yield of crops.

Another object is to lower the rate of vertical growth in plants and to provide shorter plants of more branched structure.

Yet another object is to provide a composition for inducing phytotoxic effects in noxious weeds and inhibiting or promoting germination of seeds or rhisome development.

Another object is to provide a composition suitable for fruit and foliar thinning.

Still another object of this invention is to provide a synergistic combination of components in a composition capable of generating improved plant growth regulatory effects.

Another object is to provide a process for promoting plant maturation while developing strong disease and freeze resistant plants.

These and other objects and advantages of the present invention will become apparent from the following description and disclosure.

According to the present invention there is provided a coacting plant growth regulating, ethylene inducing mixture for the treatment of crops or ornamentals and particularly for the preharvest treatment of cotton; fruit trees; sap, latex and oil bearing trees and plants of the Gramineae, Leguminosae, Solanaceae, Musaceae, Cucurbitaceae, Bromeliaceae and Rubiaceae families which contains as active ingredients a N-heterocyclic monoamide, having one hetero-nitrogen atom per ring such as N-methylpyrrolidone and polymers such as polyvinylpyrrolidone, or mixtures thereof and an ethylene generating compound, such as 2-haloethylphosphonic acid, and/or its derivatives or precursors capable of directly or indirectly generating ethylene or 2-haloethylphosphonic acid, and providing ethylene responses in plants and mixtures thereof, such as the corresponding anhydride, catechol ester or mixtures thereof wherein the halogen atom is a fluorine, chlorine, bromine or iodine atom.

The ethylene generating compounds of this invention are those containing or capable of forming the anion:

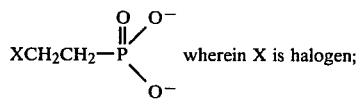

wherein X is halogen;

Of these 2-haloethylphosphonic acid, where "halo" is chloro or bromo, is preferred.

For the purposes of this disclosure, plant growth regulation is intended to include all hormonal ethylene effects including moderating, diminishing, increasing, or phytotoxic responses to normal plant growth patterns.

Th N-heterocyclic amides of the admixture are those having the formula:

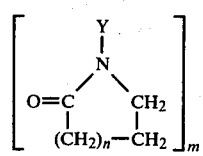

wherein Y is hydrogen, methyl, ethyl, vinyl, allyl, lower alkylhydroxy or phenyl optionally substituted with lower alkyl or halogen; n is an integer having a value of 1 or 2 and m is an integer having a value of 1 except, when Y is vinyl, m has a value of from 1 to 5,000. Examples of these amides include N-methyl-2-pyrrolidone, 2-pyrrolidone, N-methyl-2-pyridone, N-methyl-2-piperidone, N-(o-tolyl)-2-pyrrolidone, N-(2-hydroxyethyl)-2-pyrrolidone, N-isopropyl-2-pyrrolidone or polyvinylpyrrolidone. The polyvinylpyrrolidones of the mixtures include polymers containing from 2 to 5,000 monomer units having the structure:

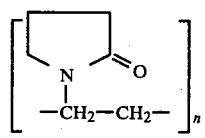

wherein n has a value of from 2 to 5,000.

Of these, N-methyl-2-pyrrolidone and polyvinylpyrrolidone of K20 to K90 are preferred; the former being most preferred.

In a preferred aspect, the present invention relates to a composition for plant growth regulation comprising an ethylene generating compound, such as 2-chloroethylphosphonic acid, the corresponding anhydride of said acid, the corresponding catechol ester of said acid or mixtures thereof which composition is improved by incorporation of a plant growth enhancing amount of N-methylpyrrolidone or a polyvinylpyrrolidone having a K value of up to about 90 and including oligomers, or mixtures of said polymers or monoamide and polymer.

The N-heterocyclic amide and 2-haloethylphosphonic acid compound are combined in a mole ratio of between about 0.005:1 and about 15:1, preferably in a mole ratio of between about 0.1:1 and about 4:1. These compounds may be applied directly to the plant as an admixture or successively as separate compounds to form said mixture on the plant or plant situs.

Although the acid and amide components can be applied in an undiluted state to a plant or plant situs, for economic reasons and for more controlled and uniform coverage, the mixture, or the components thereof, is usually employed as a composition by incorporation into an inert diluent or carrier which is preferably a liquid such as water, xylene, toluene, cyclohexane, other liquid paraffins, vegetable oil, mineral oil fractions, glycerine or other inert organic liquids, or mixtures thereof which are conventionally employed as inert carriers. The concentration of the present mixture of N-heterocyclic amide and acid in the overall composition, prepared as a spray solution, can vary between about 0.0001 ppm and about 100,000 ppm. Usually, for a plant growth regulating or maturation response, a concentration in excess of about 25,000 ppm is not required. Herbicidal responses for most plant species are generally achieved at concentrations between about 10,000 ppm and about 60,000 ppm. Also, herbicidal dosage levels are higher than those required for growth promotional effects, although some overlap may occur. Generally, for herbicidal effects, it is recommended that one use 50 ppm in excess of the dosage where an additional promotional or maturation response ceases. The liquid carrier or extender may optionally contain a conventional amount of surface active agent such as a polyoxyalkylene fatty acid ester or alcohol ether, lignin, methyl cellulose, etc. or a conventional thickener such as glycerine, guar gum, inert resins, etc.; although such is not needed to provide the herein described benefits of this invention. Also, water can be employed as a diluent with an auxiliary organic solvent which may be selected from those listed above.

It is to be understood, however, that the present mixture can also be applied to the plant as a paste, powder or granulated solid by use of extenders such as talc, bentonite clays, diatomaceous earth, Kaolins, petrolatum paste or jellies and other inert and conventional solid or semi-solid extenders in the same concentration ranges set forth for the liquid carriers.

The above composition or its components of which at least one is mixed with a carrier, is applied to a plant, plant situs or plant part by spraying atomizing, dusting, broadcasting, injecting, immersing or washing under normal or subnormal temperature conditions. Plant dosage levels desirably between about 0.0005 and about 1.3 grams of the N-heterocyclic amide, e.g. N-methylpyrrolidone per plant, preferably between about 0.001 and about 0.9 grams per plant of N-methylpyrrolidone or polyvinylpyrrolidone in the above mixture is applied to provide the desired effects.

Generally, the present composition, i.e. mixture with carrier and other adjuvants, if present, is applied to a field of crop at a rate of between about 5 and about 5,000 Kg/hectare of soil area for growth promotion or advancement of plant maturation. To obtain a phytotoxic response, the application rate required for certain persistent or deep rooted weeds may exceed 10,000 Kg/hectare, e.g. up to 12,000 Kg/hectare or more; however, a rate of from about 10 to about 8,000 Kg/hectare is usually adequate for most weed species. Control of seed germination and seedling emergence may require mixture or injection of the present composition into the soil to a depth up to 4 or 5 inches, particularly where certain deep rooted weeds are involved. When large dosages of the present mixtures or compositions are dispersed in or on the growth media, a persistent inhibition of seed germination, emergence of seedlings and development of established plants of many species is obtained. The present compositions have a substantial degree of toxicity for broad leaf plants and low toxicity for many narrow leaf plants when used in herbicidal dosages. Therefore, they can be adapted for selective control of broad leaf plants in a field of narrow leaf crops.

Thus, the concentration of the plant growth altering mixture in carrier and its rate of application can vary over a wide range depending on the species of plant or plant part, the age and health of treated plant tissue, the response desired, the climatic conditions at the time of application, the particular components of the growth altering composition and the repetition of treatment; which factors are to be considered and dealt with in a conventional manner when carrying out the plant growth regulating process in accordance with known agricultural practices.

Generally, the process of the present invention can employ between about 0.00001 ppm and 100,000 ppm, preferably between about 0.1 and about 45,000 ppm, of a composition of the above defined amide and acid mixture in a mole ratio of between about 0.005:1 and about 15:1 (2-haloethylphosphonic acid per N-heterocyclic ring of said amide), applied at a rate of from about 0.1 Kg/Ha to about 12,000 Kg/Ha by spraying, washing, dusting, broadcasting, dipping the plant or plant part, or drenching or irrigating the plant situs at a temperature of from about 20° F. to about 115° F., preferably from about 35° to about 90° F., using conventional spraying, dusting, drenching or irrigating equipment.

In the preharvest treatment of cotton for simultaneous and synchronized defoliation and dehiscence, the present mixture of components is applied after boll set. By way of illustration, in the treatment of cotton plants to provide increased yield on single harvest and synchronization of boll opening and leaf drop, application of a 2-chloroethylphosphonic acid/N-methyl-2-pyrrolidone mixture (from about 1,000 ppm to about 15,000 ppm in a carrier) is preferably effected at least 30 days after square set; although it is to be understood that application can be made at any time after the square set up through initial boll break without any damage to the plant or plant fiber and still provide beneficial effect.

The present composition is applied to the crop at a temperature desirably within the range of from about 25° F. to about 95° F.; although application at higher or lower temperatures does not result in crop damage, but merely alters the period for plant response, which is extended at lower temperatures and shortened at higher temperatures. Normally, the results of the present application are evident within 4 to 14 days after treatment depending upon the plant treated, the concentration of the active ingredients and the temperature conditions extent. For example, with low level applications, results have been observed in living plants within 8 to 12 days; whereas at high level applications, results have been evident within 4 to 7 days.

In the case of cotton, it has been found that field temperatures of about 95° F. and above generally do not require dosage levels above 3,000 ppm N-methylpyrrolidone, although higher dosage levels can be employed without damage to the plant or cotton fiber.

The advantages realized from the application of the present composition for preharvest treatment of cotton are enumerated as follows:

1. Providing a multipurpose mixture for effecting boll ripening, boll dehiscence and leaf defoliation so as to avoid the need for multiple chemical applications.
2. Increasing the rate of boll dehiscence so as to provide more uniformly opened bolls for first harvest collection and synchronizing defoliation so that it is effected after the bolls are fully developed and opening or opened.
3. Synergistic coaction between the active ingredients of the composition to produce metabolic effects in increasing dehiscence which exceeds the sum of effects obtained with the individual components.
4. Advancing early dehiscence of bolls containing mature fibers while having substantially no effect on the completely matured breaking bolls so as to increase the proportion of recoverable cotton in a single, first harvest and to minimize and/or obviate the necessity of a second harvest.

5. Providing cotton fiber of inherent high quality and, in certain cases, improving the quality of cotton fiber.
6. Reducing plant temperature sensitivity and resistance to low temperature dehiscence.
7. Permitting later planting of crop and/or earlier harvesting.
8. Providing economic and labor saving harvest of cotton crops.

The plant growth regulating composition is most desirably 2-haloethylphosphoric acid which is an ethylene generating and an ethylene—or other hormone—inducing agent and a significant amount of N-methylpyrrolidone effective to enhance said hormonal properties of ethylene or said ethylene generating agent. The molar ratio of acid to amide in this preferred composition is between about 0.1:1 and about 4:1; although it is to be understood that amounts of amide as low as 0.005 moles per mole of acid still provide some enhancing effect.

Formulations including the present compositions, namely the admixture and carrier or diluent may also include a compatible surface active agent, a thickener, and/or other agricultural chemicals such as, for example, an algicide, a fungicide, an herbicide, an insecticide, a nematocide, a disinfectant, or another plant growth regulant; or mixtures of these. When such mixtures are used, the added agricultural agents are those which do not materially lower the activity of the composition and are employed in minor amount. Exemplary of other agricultural agents which may be employed with the compositions of the present invention include tributyl-phosphortrithio-ate or -ite (DEF or FOLEX); 1,1-dimethyl-4,4'-bipyridinium salts, e.g. the methyl sulfate salt or halide salt (Paraquat); sodium chloride, an alkali metal salt of cacodylic acid, e.g. the sodium salt BOLL's-EYE; chlorinated isophthalonitriles, e.g. the tetrachlorinated derivative, Daconil; alkyl-1-(butylcarbamoyl)-2-benzimidazole carbamate, e.g. the methyl derivative, Benomyl; 2-hydroxyethylhydrazine, Omaflora; 2-chloroethyl boric acid; dialkylaminobenzenediazo alkali metal sulfates, e.g. the dimethyl derivative, Dexon; 2-bromoethyl phosphonic acid; chloroethyl tris (2-ethoxy)silane; 2,4-dinitro-6-alkylphenyl-crotonate, e.g. the actyl derivative Karathane; manganese ethyl bix(dithiocarbamate), e.g. Maneb or Manzate; 2,3-dihydro-5-carboanilido-6-methyl-1,4-oxathiin-4,4-dioxide, (Plantvax); polychloronitrobenzenes, e.g. the pentachloro derivative Terraclor; 5-ethoxy-3-trichloromethyl-1,2,4-thiadiazole, Terrazole; 5,6-dihydro-2-methyl-1,4-oxathiin-3-carboxanilide, Vitavax; tetramethylthiuram disulfide, Arasan; N-(acyl-tert.-amidoalkyl) anilides, such as Lasso; esters of cyclopropane substituted carboxylic acids; alkylsulfinyl substituted diphenylethers; alkyl-1,2-dimethyl-3,5-diphenyl pyrazolium salts and derivatives thereof; 2-haloethylsulfinic acid; diethyl- amino-2,6-dinitro-4-trifluoromethylbenzene, and its derivatives such as the amino substituted derivative Cobex; dinitroanilines; trifluoromethyl-nitro-diphenyl ethers; halo-N-cyclicimido-alkylene-substituted acetanilides; dichloronitrobenzoic acid and derivatives thereof, e.g. Dinoben; phosphonium salts, such as Phosphon; halogenated benzoic acids, such as 2,3,6-TBA or Benzac, 2,4-D and 2,4,5-T; aminodihalobenzoic acids, such as Amiben; polychlorophenyl-nitrophenylate ethers, such as Modown; 6-benzyl-aminopurine (Benzyladenine); arylazomalononitriles; dimethylformamide; methyl acetamide; dimethylacetamide; 2-propyl-2-chloroethyl-trifluoro-dinitropropyl toluidine (Basalin); N,N-bis (phosphonomethyl) glycine (Glyphosine); 5-chloro-3-methyl-4-nitro-1H-pyrazole; 2-chloroethyl-trimethyl ammonium chloride (Cycocel or CCC); 2-(3-chlorophenoxy) propionic acid (3-CPA); 4-chlorophenoxyacetic acid (4-CPA); 3-(chlorophenyl)-1,1-dimethylurea (Monuron); N-dodecyl guanidine acetate, (Dodine); urea; 2-iodo- or 2-chloroethylphosphonic acid; 3-amino-1,2,4-triazole; cycloheximide; 2-(3-chlorophenoxy) propionamide; maleic hydrazide (1,2-di-hydropyridazine-3,6-dione); ammonium thiocyanate; an alkali metal salt of 2,3-dichloro-2-methyl propionic acid, (e.g. the sodium salt, Mendok); 3-(3,4-dichlorophenyl)-1,1-dimethylurea (Diuron); 6,7-dihydrodipyrido pyrazidiunium dibromide (Diquat); maleic hydrazide; 2,4-dinitro-6-sec-butyl-phenol (Dinoseb); cycloheximide; N-2,4-dimethyl-5-(trifluoromethyl)-sulfonylamino phenyl acetamide (Mefluidide); haloalkyl silanes; 6-furfurylaminopurine (Kinetin); 4-hydroxyethyl-hydrazine (BOH); 1-hydroxytriacontane; 3-indoleacetic acid (IAA); 3-indolebutyric acid (IBA); abscisic acid (ABA); 1-naphthaleneacetic acid (NAA); dieldrin-hexachloro-epoxy-octahydro-endodimethan-naphthalene (Endrin); 2-haloethylthiosulfinic acid or its anhydride; the 2,4-dichlorophenol ester of benzene (Genite); N-[(tetrachloroethyl) thio]-4-cyclohexene-1,2-dicarboximide, (Difolatan 4F); monosodium acid-methane arsonate (MSMA); trichlorophenyl-acetic acid alkali metal salt (Fenac); 2-naphthoxyacetic acid (BNOA); the alkyl amine salt of succinic acid or of 7-oxabicycloheptane-2,3-dicarboxylic acid (Endothall); succinic acid-2,2-dimethyl hydraine (SADH or Alar); gibberellic acid (Activol or Gibrel); 2,3,5-triiodo benzoic acid (TIBA); iron chelate; sulfur; nicotine sulphate; lead arsinate; self-emulsifying petroleum oil; sodium selenate; zinc ethylene bisdithio-carbamate (Zineb); tetramethyl thiuramdisulfide (THIRAM); N-trichloromethyl thiotetrahydrothalimide (Captan); mercaptobenzolthiozole (Rotax); 1,1,1-trichloro-2,2-bis(chlorophenyl) ethane (DDT); 2-(2,4,5-trichlorophenoxy) propionic acid (Silvex); 3,6-dichloro-o-anisic acid (Dicamba); 2,2-dichloropropionic acid (Dalapon); 2-chloro-4,6,-bis(ethylamino) -S-triazine (Simazine); N,N-diallyl-2-chloroacetamide (CDAA); 2-chloroalkyldiethyl-dithio carbamate (CDEC); dimethyltetrachloro-teraphthalate (DCPA or Dacthal); N,N-dimethyl-2,2-diphenyl acetamide (Diphenamide); dimethyldithiocarbamate (Ferbam or Ziram); malathion; actidione, copper or zinc dimethyldithiocarbamate (Ziram); hexahydromethanoindene (Chlorodane); chlorinated dimethano naphthalene (Dieldrin or Aldrin); potassium or sodium N-methyl dithio-carbamate dihydrate (Vapam); 2,2-dichlorovinyl dimethyl phosphate (Vapona or DDVP); O-(2,4-dichlorophenyl)-O-methyl isporopyl phosphoramidothiate (Zytron); arsenic trioxide mixtures (Sodite); posphomolybdic acid (PMA); O,O-diethyl-O(2-isopropyl-6-methyl-4-pyrimidinyl) phosphorothioate (Diazinon); 1,1-bis(chlorophenyl)-2,2,2-trichlorethanol (Kelthane); 2,2-bis(p-methoxyphenyl)-1,1,1-trichloroethane (Methoxychlor or DMDT); 2,4,4',5-tetrachlorodiphenylsulfone (Tedion); trichloro- or tetrachloro- isophthalonitrile (chlorothalinol); O,O-diethyl-O- (and S-)-2-(ethythio) ethyl phosphorothioates (Systox); isopropyl-N-(3-chlorophenyl) carbamate (chloro-IPC or CIPC); sodium 2,4-dichloro-phenoxyethylsulfate (SES or Sesone); Bordeau mixture; preparations containing streptomycin (Agrimycin); N-trichloromethylthiophthalimide (Phaltan); Cis-N-[(1,1,2,2-tetrachloroethyl) thio]-4-cyclohexene-1,2-dicarboximide, (captafol); ethyl mercuric chloride mixtures, (Ceresan); 3,5-dimethyl-2H-1,3,5-tetrahydro-thiadiazine-2-thione, (Mylone); 1-naphthyl-N-methylcarbamate, (Carbaryl); 1-dimethyl-carbamoyl-5-methyl-3-pyrazolyl dimethylcarbamate, (Dimethilane); O,O-dimethyl S-(N-methylcarbamoyl methyl) phosphorodithioate, (Dimethoate); 3-(3,4-dichlorophenyl)-1-methoxy-1-methylurea, (Linutron); 2-chloro-4,6-bis(ethylamino)-S-triazine, (Simazine); 1,2-bis(3-ethoxycarbonyl)-2-thioureido) benzene, (thiophanate); 1,1,1-trifluroro-2,6-dinitro-N,N-dipropyl-p-toluidine, (Treflan or Trifluralin); 4-dimethylamino-3,5-xylyl N-methylcarbamate, (Zectran); ferric dimethyl dithiocarbamate, (Ferbam); N-1-naphthyl phthalamic acid, (NPA); S-propyl-butylethyl thiocarabamate, (PEBC); disodium methane arsenate (sodar); calcium acid methyl arsinate (carlar); -benzenehydrochloride (Lindane); diethyl-S-diethylamino ethyl phosphorthiolate (Amiton or Amitrole); rotenone; pyrethrum; the acaricide of 2,4,5,4'-tetrachlorodiphenyl sulfone (Tedion);1,1-dimethyl-piperidinium salts, e.g. Metiquat chloride and Terpal; the anionic salts of allyltrimethylammonium-, bromoethyltrimethylammonium-, isopropyltrimethylammonium-, N-chlorethyl-N,N-dimethyl-hydrazonium-, N-bromoethyl-N,N-dimethydrazonium-, N-isopropyl-N,N-dimethylhydrazonium-, N-allyl-N,N-dimethylhydrazonium-and N,N-dimethylmorpholinium- cations and many more plant growth regulators and agricultural agents. Each of the above active adjuvants is individually effective at a range of rates, depending upon the particular substance, the particular use and the type of plant or soil and other growing conditions. Generally, these substances are employed individually at rates of between 0.001 and about 40 lbs. per acre. The same rate of application can be employed in the present invention when such chemically active additives are administered separately. When employed in admixture with the compounds of the present invention, or with either of separate solutions of the amide of the present mixture or the haloalkylphosphonic acid solution, the known agent is preferably incorporated in an amount between about 0.01 weight percent and about 60 weight percent, based on the weight of the total composition. It is generally preferred that the known agricultural agent be used in an amount within its established rate range for individual use as sole agent, although because of the combined effect attributable to the present compounds, lesser amounts within the established rate range or amounts below the established rate range are appropriate. Thus, amounts below the median of the established rate range generally give good results in combination with the present mixtures, particularly the chloroethylphosphonic acid/methylpyrrolidone mixture.

The compounds and/or compositions of the present invention can be employed for plant growth regulation purposes on many plants including gymnosperms and angiosperms, of monocotyledonous and dicotyledonous types. Species of these embrace vegetables, fruits, grasses, shrubs, trees, ornamentals and the like. Examples of plant life which can be treated with the present mixtures alone in combination with a carrier, thickener or other inert or in admixutres with other agricultural chemicals include fruit trees, such as apple, peach, apricot, tangerine, pear, cherry, grapefruit, orange, lemon, lime, plum, persimmon, banana, guava, nectarine, olive, papaya, date, fig, oak, hazel, beach, pecan, almond, rubber, cork, pine, elm, spruce, fir, cedar, yew, eucalyptus, magnolia, dogwood, palm, walnut, willow, avacodo, chestnut, hawthorn, maple, mango, and the like, as well as the fruits thereof. Examples of vegetables suitably treated with the present mixtures, compositions or admixtures include asparagus, beans, brussel-sprouts, carrots, cauliflower, celery, cucumber, squash, lentil, lettuce, onion, peas, peanut, peppers, potatoes, pumpkin, soybean, spinach, tomato, broccoli, kale, beets, and the like. Examples of grains and grasses which may be treated with the present mixtures, compositions or admixtures include barley, rye, oats, wheat, rice, corn, bluegrass, clover etc. Ornamentals suitably treated include rhododendron, rose, azelea, tulip, carnation, chrysanthemum, dahlia, basil, rosemary, whisteria, clematis, hyacinth, geranium, impatien, iris, lily, poinsetta, snapdragon, fuchia, gladiola, sweet pea, zinnia, phlox, etc. Other crops suitably treated with the present compounds or their admixutres include pineapple, melon, grapes, hops, berries, such as cranberries, strawberries, raspberries, boysenberries, blueberries, blackberries and currants, coffee plants, sugar cane, flax, cotton, tobacco plants and the like.

The compounds of the present invention induce the plant growth regulating effects generally associated with hormonal ethylene activity, but to a significantly higher degree of response, such as control of apical dominance and promotion of branching, bud initiation and enlargement, callus induction, increased resistance to cold, color and ripening promotion, breaking dormancy in seeds, rhisomes, corms, etc., inhibition of stem elongation; increased flowering and fruit set, advance to harvesting, increasing transpiration and translocation, increasing sap flow, rooting, resistance to lodging, disease resistance, loosening of fruit and nuts, dehiscence, defoliation, female sex expression of flowers, promotion of rooting and rhizome development, cell elongation, intermodal elongation, nodal development and elongation of grass spikelets for cutting and promotion of sprigging of panicoideae and festucoideae grasses, seed development, increased yield in crops and other effects more fully discussed on pages 103 through 233 of Ethylene in Plant Biology of Frederick B. Abeles, published by Academic Press, 1973 and on pages 1217 through 1316 of BIOCHEMISTRY AND PHYSIOLOGY OF PLANT GROWTH SUBSTANCES (supra). The present mixture is also useful as a herbicide or herbicidal aid to control or eradicate growth and prevent regrowth of noxious weeds and plant generation in unwanted areas. The herbicidal effects are obtained with extrapromotional dosages of the present mixture and may be as high as 75 pounds/acre, more commonly dosages of up to 30 pounds/acre. Herbicidal agents are preferably applied before seed production and most preferably before flowering. The exact dosage is dependent upon such factors as the plant species to be controlled; the stage of development, e.g. seed, immature seedling, matured plant or reproducing plant; rainfall, temperature, method of application whether applied by foliar contact, dispersion in the soil and type of soil, repetition of treatment; etc. Generally for a herbicidal dosage the concentration of the present mixture is at least 50 ppm in excess of that level of concentration where no additional promotional or maturation response is effected. As an example, a herbicidal effect for many plants is reached at concentrations between about 5,000 ppm and about 45,000 ppm and the herbicidal dosage is applied at between about 1 and about 25 pounds per acre, in the form of an aqueous spray or dust or is broadcast over an area in the form of course gains or pellets.

Types of weeds that can be controlled by the present mixture include millet, mesquite, poison ivy, huisache, witchweed, ragweed, members of the genus Amaranthus such as pigweed, the genus Agropyron such as quackgrass, the genus Mollugo such as carpetweed, the genus Taraxacum such as dandelion, the genus Plantago such as plantain, the genus Stellaria such as chickweed, the genus Chenopodium such as lambsquarters, the genus Polygonum such as smartweed, the genus Sorghum such as Johnson grass, the genus Digitaria such as crabgrass, foxtail, the genus Helianthus such as sunflower, the genus Centaurea such as thistle, the genus Cynodon such as Bermuda grass, and broad leaf grasses.

Higher dosages for herbicidal use of the present mixture can be effected by applying 2-chloroethylphosphonic acid or 2-bromoethylphosphonic acid and the N-heterocyclic amide to a plant in several ways. For example, an initial low level application can be made at about the outset of flower budding or at the seed germination phase of the plant, so as to synchronize and hasten the development of seed heads or the germination of seedlings, followed by a later, heavier herbicidal dose to kill 50%–90% of the seeds or seedlings with a single herbicidal treatment. Other methods of control involve immediate killing of the weed by applying a phytotoxic dose to cause total defoliation, to kill the cambrium layer around the plant stem, to cause aberrant tissue formation, or to cause phloem hypertrophy and gummosis, or any combination of these effects.

Having thus generally described the invention, reference is now directed to the following Examples I through XXXV and XLIV through XCV which serve to illustrate preferred embodiments and advantages of promotional plant growth regulation or maturation, and to Examples XXXVI through XLIII which illustrate preferred herbicidal applications and advantages derived therefrom. However, these examples are not be be construed as limiting to the scope of the invention as more generally set forth hereinabove and as defined in the appended claims. In the examples all amounts and proportions are by weight unless otherwise indicated.

EXAMPLE I

The experiments reported in Table I are comparative examples illustrating the % boll opening, including half-open, open and harvestable bolls, obtained with untreated plants (A), with N-methylpyrrolidone and ethephon compositions at various concentration levels (B), with a propylene glycol and ethephon composition (C), with N-methylpyrrolidone as the sole active ingredient (D), and with ethephon as the sole active ingredient (E), in aqueous solutions.

Each of four groups, B'-E', of five 12-week old Gossypium barbadense plants from the same seed source, grown in sterilized soil in 12" clay pots under uniform conditions, were treated with one of the four aqueous solutions B-E above in a growth regulating formulation. A separate group of plants, Group A', was reserved as a control. Specifically, Group A' represents untreated plants; Group B' represents plants treated with compositions of N-methylpyrrolidone and ethephon; Group C' represents plants treated with a propylene glycol/ethephon mixture; Group D' with N-methylpyrrolidone alone and Group E' represents plants treated with ethephon alone as the active ingredient. The components of the formulations are reported in ppm in a liter of aqueous solution. These tests were carried out simultaneously and an average temperature of about 21° C. day and 13° C. night temperature was maintained in the growth chamber.

TABLE I

% Boll Opening Study

| COMPOSITION* | NMP | E | PG | Days After Spraying |||||||||||
|---|---|---|---|---|---|---|---|---|---|---|---|---|---|---|
| | | | | 5 | 6 | 7 | 8 | 9 | 10 | 11 | 12 | 13 | 14 | 15 |
| Control A | 0 | 0 | 0 | 0 | 0 | 9 | 27 | 36 | 36 | 36 | 36 | 36 | 36 | 36 |
| Composition B | 1172 | 3125 | 0 | 23 | 54 | 62 | 78 | 78 | 85 | 100 | | | | |
| | 2344 | 3125 | 0 | 0 | 0 | 0 | 40 | 60 | 81 | 90 | 100 | | | |
| | 9376 | 3125 | 0 | 0 | 0 | 17 | 42 | 58 | 58 | 92 | 100 | | | |
| Composition C | 0 | 3125 | 4688 | 17 | 23 | 30 | 46 | 54 | 54 | 54 | 62 | 62 | 62 | 77 |
| Composition D | 2344 | 0 | 0 | 0 | 0 | 0 | 0 | 0 | 0 | 0 | 0 | 0 | 0 | 0 |
| Composition E | 0 | 3125 | 0 | 0 | 7 | 27 | 46 | 53 | 74 | 87 | 93 | 93 | 100 | |

*NMP represents N—methylpyrrolidone
E represents Ethephon
PG represents Propylene Glycol Table II reports the relative rate of N-methylpyrrolidone/ethephon compositions compared with ethephon alone and ethephon/propylene glycol on boll opening at 8, 10 and 11 days after spraying. The data obtained from these experiments was used to plot the curves shown in Graph 1. On the Graph, O represents 100% ethephon (3125 ppm) as the active ingredient in aqueous solution. To this solution, increasing amounts of N-methylpyrrolidone are added as noted along the axis of abscissa or X-axis of the graph. The curve shows a sharp increase in the relative rate of boll response when N-methylpyrrolidone is added to ethephon, i.e. from about 40–50% plant response when the active ingredient is 100% ethephon to 100% response when the active ingredient are about 2,250 ppm N-methylpyrrolidone and 3125 ppm ethephon.

TABLE II

Relative Rate of Boll Opening

| COMPOSITION | NMP | E | PG | Days After Spraying |||
|---|---|---|---|---|---|---|
| | | | | 8 | 10 | 11 |
| Control A | 0 | 0 | 0 | 0.35 | 0.42 | 0.36 |
| Composition B | 1172 | 3125 | 0 | 1.00 | 1.00 | 1.00 |
| | 2344 | 3125 | 0 | 0.51 | 0.94 | 0.90 |
| | 9376 | 3125 | 0 | 0.54 | 0.68 | 0.92 |
| Composition C | 0 | 3125 | 4688 | 0.59 | 0.64 | 0.54 |
| Composition E | 0 | 3125 | 0 | 0.59 | 0.87 | 0.87 |

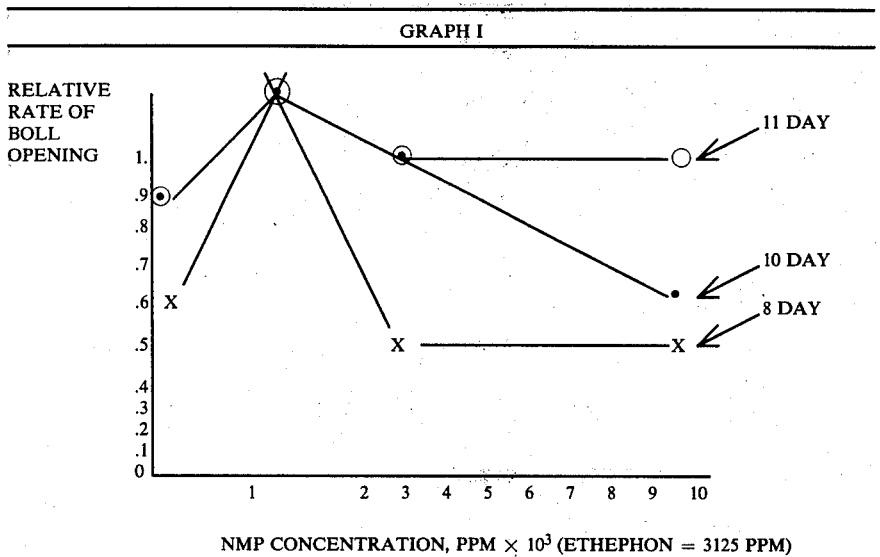

EXAMPLE II

The data reported in Table III provide comparisons based on the % of harvestable bolls obtained with each of the above compositions B through E and Control A. The harvestable bolls are those which are completely opened with the boll valves turned ownward for full exposure of the cotton fiber to the pickers.

The data reported in Table IV provides comparisons based on the relative rate of advancement to harvestable bolls obtained with compositions B, C and E and Control A above. The notations in Graph II are similar to those in Graph I, except that in the present case, the relative rate of only harvestable bolls is measured and the curves are altered to illustrate this effect.

The plant work up and treatment with compositions B through E and Control A is the same as that described in Example I, except that the observations on the days after spraying is confined to the period when the harvestable bolls are predominant (i.e. 10th–13th day after spraying).

TABLE III

| | % Harvestable Bolls | | | Days After Spraying | | |
|---|---|---|---|---|---|---|
| COMPOSITION | NMP | E | PG | 10 | 12 | 13 |
| Control A | 0 | 0 | 0 | 36 | 36 | 36 |
| Composition B | 1172 | 3125 | 0 | 39 | 54 | 54 |
| | 2348 | 3125 | 0 | 50 | 80 | 100 |
| | 9376 | 3125 | 0 | 25 | 67 | 67 |
| Composition C | 0 | 3125 | 4688 | 23 | 31 | 31 |
| Composition D | 2344 | 0 | 0 | 0 | 0 | 0 |
| Composition E | 0 | 3125 | 0 | 27 | 40 | 40 |

TABLE IV

| | Relative Rate of Promotion to Harvestable Bolls | | | Days After Spraying | | |
|---|---|---|---|---|---|---|
| COMPOSITION | NMP | E | PG | 10 | 12 | 13 |
| Control A | 0 | 0 | 0 | 0.72 | 0.45 | 0.36 |
| Composition B | 1172 | 3125 | 0 | 0.78 | 0.68 | 0.54 |
| | 2344 | 3125 | 0 | 1.00 | 1.00 | 1.00 |
| | 9376 | 3125 | 0 | 0.50 | 0.84 | 0.67 |
| Composition C | 0 | 3125 | 4688 | 0.46 | 0.39 | 0.31 |
| Composition E | 0 | 3125 | 0 | 0.54 | 0.50 | 0.40 |

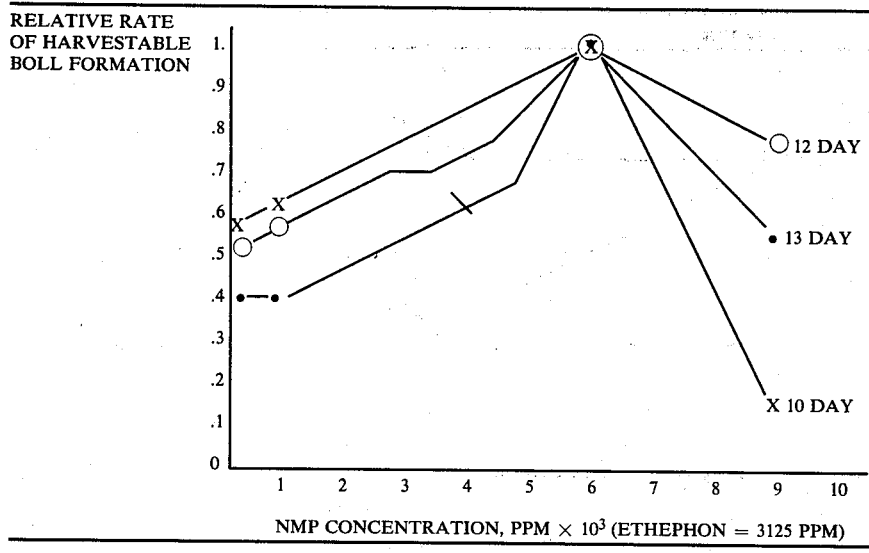

GRAPH II

RELATIVE RATE OF HARVESTABLE BOLL FORMATION

NMP CONCENTRATION, PPM × 10³ (ETHEPHON = 3125 PPM)

EXAMPLE III

The data reported in Table V provides comparisons based on the % of total boll activity, including cracking, opening, opened and harvestable bolls, obtained with each of the above compositions B through E and Control A above.

The data reported in Table VI provides comparisons based on the relative rate of total boll activity obtained with compositions B, C and E and Control A above. The notations used in Graph III are similar to those employed in Graphs I and II, except that, in the present case, the relative rate of total boll activity is plotted along the Y-axis. The plant work-up and treatment with compositions B, C and E is the same as that described in Example I. In the present case the curves of the graph are adjusted to illustrate the effect of relative rate of total boll activity.

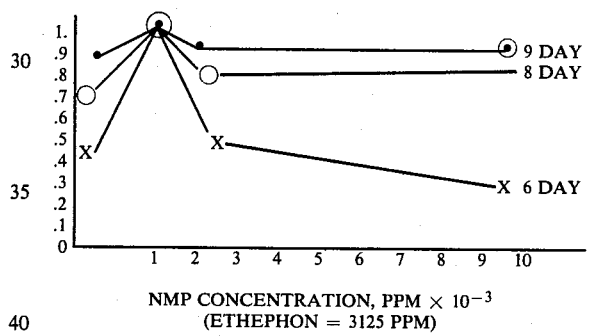

GRAPH III
RELATIVE RATE OF BOLL ACTIVITY

NMP CONCENTRATION, PPM × 10⁻³ (ETHEPHON = 3125 PPM)

TABLE V

| | | | | % Total Boll Activity | | | | | | | | | |
|---|---|---|---|---|---|---|---|---|---|---|---|---|---|
| | | | | | | | | | Days After Spraying | | | | |
| COMPOSITION* | NMP | E | PG | 5 | 6 | 7 | 8 | 9 | 10 | 11 | 12 | 13 | 14 |
| Control A | 0 | 0 | 0 | 0 | 9 | 27 | 45 | 45 | 45 | 45 | 45 | 45 | 45 |
| Composition B | 1172 | 3125 | 0 | 54 | 61 | 77 | 78 | 100 | | | | | |
| | 2344 | 3125 | 0 | 0 | 30 | 40 | 60 | 90 | 100 | | | | |
| | 9376 | 3125 | 0 | 8 | 17 | 42 | 67 | 91 | 100 | | | | |
| Composition C | 0 | 3125 | 4688 | 23 | 31 | 45 | 54 | 54 | 62 | 70 | 85 | 85 | 100 |
| Composition D | 2344 | 0 | 0 | 0 | 0 | 0 | 0 | 0 | 0 | 0 | 0 | 0 | 0 |
| Composition E | 0 | 3125 | 0 | 7 | 27 | 47 | 53 | 87 | 100 | | | | |

TABLE VI

| | Relative Rate of Total Boll Activity | | | | | |
|---|---|---|---|---|---|---|
| | | | | Days After Spraying | | |
| COMPOSITION | NMP | E | PG | 6 | 8 | 9 |
| Control A | 0 | 0 | 0 | 0.15 | 0.58 | 0.45 |
| Composition B | 1172 | 3125 | 0 | 1.00 | 1.00 | 1.00 |
| | 2344 | 3125 | 0 | 0.49 | 0.77 | 0.90 |
| | 9376 | 3125 | 0 | 0.28 | 0.86 | 0.91 |
| Composition C | 0 | 3125 | 4688 | 0.51 | 0.69 | 0.54 |
| Composition E | 0 | 3125 | 0 | 0.44 | 0.68 | 0.87 |

EXAMPLE IV

The data reported in Table VII provides comparisons based on % of leaf drop obtained with each of the compositions B through E and Control A above.

The data reported in Table VIII provides comparisons based on the relative rate of leaf drop obtained with compositions B, C and E and Control A above. Again, the notations in Graph IV are similar to those used in the preceeding graphs, except that, in this case the relative rate of leaf drop is plotted along the Y axis. The plant work up and treatment with compositions B, C and E and Control A is the same as that described in Example I. In the present case, leaf drop was plotted and the curves are altered to illustrate this effect.

TABLE VII

| COMPOSITION* | NMP | E | PG | \multicolumn{9}{c}{% Leaf Drop Days After Spraying} |
|---|---|---|---|---|---|---|---|---|---|---|---|---|
| | | | | 2 | 3 | 4 | 5 | 6 | 7 | 8 | 9 | 10 |
| Control A | 0 | 0 | 0 | 13 | 13 | 16 | 17 | 17 | 20 | 25 | 25 | 25 |
| Composition B | 1172 | 3125 | 0 | 17 | 26 | 51 | 51 | 64 | 65 | 71 | 84 | 87 |
|  | 2344 | 3125 | 0 | 29 | 31 | 53 | 57 | 74 | 95 | 96 | 98 | 98 |
|  | 9376 | 3125 | 0 | 10 | 12 | 49 | 63 | 82 | 90 | 90 | 97 | 97 |
| Composition C | 0 | 3125 | 4688 | 14 | 18 | 39 | 44 | 55 | 63 | 69 | 72 | 75 |
| Composition D | 2344 | 0 | 0 | 8 | 10 | 13 | 18 | 18 | 25 | 26 | 26 | 26 |
| Composition E | 0 | 3125 | 0 | 31 | 43 | 74 | 81 | 88 | 90 | 93 | 94 | 95 |

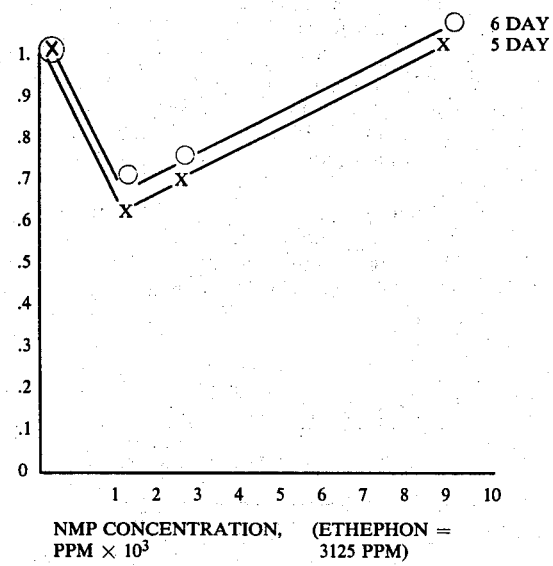

GRAPH IV
RELATIVE RATE OF LEAF FALL

NMP CONCENTRATION, PPM × 10³ (ETHEPHON = 3125 PPM)

TABLE VIII

| Composition | NMP | E | PG | \multicolumn{3}{c}{Relative Rate of Leaf Drop Days After Spraying} |
|---|---|---|---|---|---|---|
| | | | | 4 | 5 | 6 |
| Control A | 0 | 0 | 0 | 0.21 | 0.21 | 0.20 |
| Composition B | 1172 | 3125 | 0 | 0.69 | 0.63 | 0.68 |
|  | 2344 | 3125 | 0 | 0.72 | 0.71 | 0.84 |
|  | 9376 | 3125 | 0 | 0.66 | 0.78 | 0.93 |
| Composition C | 0 | 3125 | 4688 | 0.53 | 0.54 | 0.61 |
| Composition E | 0 | 3125 | 0 | 1.00 | 1.00 | 1.00 |

Two additional compositions were prepared for testing in the manner set forth for compositions B through E above. These additional compositions were prepared by mixing 2344 ppm of methyl cellosolve acetate in an aqueous solution 3125 ppm ethephon (Composition F) and 7000 ppm of S, S, S—tributylphosphorotrithioate in an aqueous solution also containing 3125 ppm ethephon (Composition G). However, compositions F and G killed the plants 3 days after application.

EXAMPLE V

The following experiments reported in Tables IX and X illustrate the effects of high temperature on cotton plant dehiscence response.

A. Three groups of 12 week old Gossypium barbadense plants from the same seed source grown in sterilized soil in 12" clay pots were tested in a growth chamber for boll opening and leaf drop; Group A' represents the control with no chemical application; Group B' represents cotton plants sprayed with the present composition (B) and Group C' represents cotton plants sprayed with a composition of ethephon and propylene glycol (C). The results reported in Table IX represent the average of 4 replicate tests for each group carried out simultaneously. The weather conditions simulated in the growth chamber imposed 81° F. day temperature and 60° F. night temperature.

The plants undergoing testing in pots were placed on an elevated grid to insure uniform temperature and humidity conditions. Aqueous solutions containing the compositions of Groups B and C in the concentrations reported in ppm were made up and applied as a uniform overhead spray to the 12 week old cotton plants at a temperature of about 70° F. and the results of these chemical applications were observed and reported on the 3rd and 5th day after spraying. The degree and type of response are presented in Table IX.

TABLE IX

| | \multicolumn{3}{c}{% Boll Opening} | \multicolumn{2}{c}{DAYS AFTER SPRAYING} |
|---|---|---|---|---|---|
| | NMP PPM | PG PPM | ETHEPHON PPM | 3RD DAY | 5TH DAY |
| Control A | 0 | 0 | 0 | 10 | 20 |
| Composition B | 2340 | 0 | 1560 | 0 | 30 |
|  | 4688 | 0 | 3125 | 50 | 50 |
| Composition C | 0 | 2340 | 1560 | 0 | 0 |
|  | 0 | 4688 | 3125 | 25 | 50 |

It is noted that higher temperature induced quicker dehiscence response.

B. Further testing of the compositions was carried out in a greenouse at 95° F. day temperature and 65° F. night temperature. The results of these tests on the fifth day after spraying are reported in Table X.

Like those in part A, these tests were also carried out in replicate groups of 4 for each test composition.

TABLE X

| | \multicolumn{3}{c}{% Boll Opening} | |
|---|---|---|---|---|
| | NMP PPM | PG PPM | ETHEPHON PPM | 5th DAY AFTER SPRAYING |
| Control A | 0 | 0 | 0 | 58 |
| Composition B | 2340 | 0 | 1560 | 80 |
|  | 4688 | 0 | 3125 | 75 |
| Composition C | 0 | 2340 | 1560 | 70 |
|  | 0 | 4688 | 3125 | 70 |

As shown above, boll opening is greatly accelerated in the control and by Composition B at 95° F.

Composition B advanced boll opening in unripe bolls containing matured fibres, but did not affect the thoroughly matured breaking bolls. There was no degradation of fiber from the fully matured bolls treated with Composition B and the dehiscence induced in the immature bolls improved fiber quality by reducing dormancy inside the boll and potential time for fungus infection and by inducing boll opening prior to defoliation and increasing the rate of boll development at a higher plant vitality before defoliation interrupts photosynthesis.

EXAMPLE VI

The comparisons reported in Table XI illustrate the effect of low temperature found on cotton plant dehiscence response in the field.

Field tests were carried out on a 50 cm plant-to-plant spacing of 12 week old cotton plants of the Gossypium Hirsutum variety using an untreated control group A (2 rows of 50 plants each); the same number of plants treated with Composition B (Group B'), the same number of plants treated with Composition C (Group C') and the same number of plants treated with N-methylpyrrolidone alone Composition D (Group D'). The temperature varied from 40° F. day temperature to 25° F. night temperature. Results are reported in Table XI.

TABLE XI

|  | NMP PPM | PG PPM | ETHEPHON PPM | DAYS AFTER SPRAYING 6 | 8 |
|---|---|---|---|---|---|
|  |  | % Boll Cracking |  |  |  |
| Control A | 0 | 0 | 0 | 0 | 7 |
| Composition D | 9375 | 0 | 0 | 0 | 0 |
| Composition C | 0 | 4688 | 3125 | 22 | 26 |
| Composition B | 4688 | 0 | 3125 | 43 | 52 |

In the above tests of Table XI it is seen that composition B greatly lessens normal low temperature plant resistance to boll cracking. At 3125 ppm ethephon concentrations, Composition B induces significantly less plant low temperature sensitivity than does Composition C. The effects of defoliation were not determinative because of below freezing temperatures which induce natural defoliation, accordingly no measurement of this effect was made.

In all of the above experiments, cotton plants sprayed with Composition B suffered no weakening or shortening of fiber. Staining both before and after harvest was virtually eliminated and later developing bolls where dehiscence was induced with the present composition, actually produced better fiber.

It can readily be appreciated from the above data that the present composition of N-methylpyrrolidone and B-haloethylphosphonic acid provides a multipurpose tool for harvesting cotton in obviating the need for separate chemical defoliant and dehiscence applications and that the rates of these metabolic effects are more efficiently utilized to provide a higher yield of better quality cotton with a single harvesting.

The synergistic coaction of the active ingredients are also evident from the data as well as the potential yield increase for first harvest. Optimum combinations of the present ingredients within the above ranges can be made to meet the needs of a particular cotton crop and obviate the need for second harvest.

The commercial benefits of the present composition and process of labor saving application to cotton crops, in permitting later planting and/or earlier harvest in the natural rotation of crops, are self-evident.

It is to be understood that, in the foregoing Examples, any of the other aforementioned B-haloethylphosphonic acids can be substituted for B-chloroethylphosphonic acid in achieving the benefits prescribed by this invention.

Also, in the above examples, a noncyclic tertiary amide of from 3 to 6 carbon atoms, e.g. N,N-dimethyl formamide, N,N-dimethylacetamide, etc. may augment N-methylpyrrolidone to provide an increased rate of defoliation prior to harvest.

These amides and other compounds reported in the following Table XII were found to have high defoliating properties when applied to cotton plants. The amounts reported to Table XII for the respective components of the compositions employed are in parts per million.

It will become apparent that any of the following compounds or compositions can be used alone or in combination with the present N-methylpyrrolidone/ethephon composition to enhance defoliation in cotton plants.

TABLE XII

|  | E | BLO[1] | MCA[2] | DMF[3] | % Leaf Drop Days After Spraying | | | | | | | | |
|---|---|---|---|---|---|---|---|---|---|---|---|---|---|
|  |  |  |  |  | 2 | 3 | 4 | 5 | 6 | 7 | 8 | 9 | 10 |
| Control | 0 | 0 | 0 | 0 | 13 | 13 | 16 | 17 | 17 | 20 | 25 | 25 | 25 |
|  | 3125 | 2344 | 0 | 0 | 29 | 45 | 62 | 68 | 72 | 82 | 82 | 92 | 98 |
|  | 3125 | 0 | 2344 | 0 | 23 | 32 | 60 | 66 | 84 | 88 | 97 | 100 |  |
|  | 3125 | 0 | 0 | 2344 | 46 | 56 | 83 | 85 | 91 | 99 | 100 |  |  |

[1]Butyrolactone
[2]Methyl cellosolve acetate
[3]N,N—dimethylformamide

The following data illustrates the effect of butyrolactone (BLO)-Ethephon, butynediol (B$_3$D)-Ethephon and dimethylformamide (DMF)-Ethephon on cotton boll activity in 15 week-old cotton plants of the Gossypium Hirsutum variety.

Four replicate plants in a growth chamber were employed for each of the above mixtures in aqueous solution and each plant was sprayed to drench at 68° F. The % of total boll activity (including boll cracking, boll opening and harvestable bolls) is reported in Table XIII.

Table XIV reports the % of harvestable bolls for each of the aqueous solutions of the above mixtures.

In Tables XIII and XIV the amounts of components employed are reported in parts per million in aqueous solution.

TABLE XIII

|  | E | BLO | B$_3$D | DMF | % Total Boll Activity Days After Spraying | | | | | |
|---|---|---|---|---|---|---|---|---|---|---|
|  |  |  |  |  | 5 | 6 | 7 | 8 | 9 | 10 |
| Control | 0 | 0 | 0 | 0 | 20 | 20 | 20 | 20 | 20 | 20 |
|  | 3125 | 2344 | 0 | 0 | 50 | 65 | 75 | 88 | 88 | 88 |
|  | 3125 | 0 | 2344 | 0 | 86 | 100 |  |  |  |  |
|  | 3125 | 0 | 0 | 2344 | 71 | 86 | 72 | 72 | 72 | 72* |

*14% bolls abscised after 6 days

TABLE XIV

| | E | BLO | B₃D | DMF | % Harvestable Bolls Days After Spraying | | | | | |
|---|---|---|---|---|---|---|---|---|---|---|
| | | | | | 5 | 6 | 7 | 8 | 9 | 10 |
| Control | 0 | 0 | 0 | 0 | 0 | 20 | 20 | 20 | 20 | 20 |
| | 3125 | 2344 | 0 | 0 | 37 | 37 | 50 | 63 | 75 | 88 |
| | 3125 | 0 | 2344 | 0 | 58 | 72 | 86 | 93 | 100 | |
| | 3125 | 0 | 0 | 2344 | 57 | 72 | 72 | 72 | 72* | |

*14% bolls abscised after 6 days

The present coacting mixtures are also beneficially employed as plant growth regulants for other plants as illustrated by the following plant species of Examples VIII through XVIII.

EXAMPLES VII–X

A field test was made as a comparison between an equimolar mixture of N-methylpyrrolidone (NMP) and 2-chloroethylphosphonic acid and 2-chloroethylphosphonic acid (CEPA) per se in their relative ability to cause mature, green, flue-cured tobacco leaves to turn yellow and ripen. The results of this study are given in the following Table XV.

In the field, 8 separate plots averaging 50 tobacco plants each, growing under the same conditions, were reserved for testing. The first two plots were sprayed with an aqueous solution of CEPA at a rate of 0.00687 lb. mole/acre and the results averaged and reported as Plot #1. Another two plots were also sprayed with an aqueous solution of CEPA at a rate of 0.01374 lb. mole/acre (i.e. the standard commercial rate employed for CEPA) and the results averaged and reported as Plot #2. An additional two plots were sprayed with an aqueous solution of the equimolar mixture of NMP/CEPA at a rate of 0.00746 lb. mole/acre and the results averaged and reported as Plot #3. The final two plots were left untreated and reported as the control.

TABLE XV

| Example Number | Plot Number | CEPA* lb. mole/Acre | CEPA*/NMP 1:1 MIXTURE lb. mole/acre | Days after treatment to produce a harvestable crop | Yield of cured Tobacco lb./acre |
|---|---|---|---|---|---|
| VII | 1 | 0.00687 | 0 | 15 | 2610 |
| VIII | 2 | 0.01374 | 0 | 4 | 2105 |
| IX | 3 | 0 | 0.00746 | 4 | 2250 |
| X | Control | 0 | 0 | 21 | 2650 |

*CEPA is 2-chloroethylphosphonic acid (Ethephon)
NMP is N—methyl-2-pyrrolidone

It is highly significant that the treatment with the present equimolar mixture gave a 7% increase in yield over 2-chloroethyl phosphonic acid, (plot #2), which is the standard commercial rate for 2-chloroethyl phosphonic acid, and also provided a ripened harvestable crop within a quarter of the time required for CEPA, when CEPA and the mixture are applied at substantially the same rate.

When the 1:1 molar mixtures of NMP/CEPA and N-methyl piperidone/CEPA in a concentration of about 3,000 ppm in aqueous solution are sprayed to run off on rangy plants during their growing stage (e.g. an ornamental such as chrysanthenums or a member of the grass family such as corn), noticeable stunting (10–25%) of the mature plant results. The mixtures of this invention provide many of other plant growth regulating effects which are known and are attributed to ethylene. These results are realized by the enhanced ethylene generating or ethylene inducing affects of the present mixtures.

EXAMPLE XI

Apple Reddening

Four replicate groups of Cornell McIntosh fruit bearing apple trees were sprayed to run-off with the aqueous solutions noted in Table XVI. Another replicate group of trees was left untreated as a control. After one week, the apples were harvested and physical measurements taken. The replicate results were averaged and reported as follows:

TABLE XVI

| Treatment | Rate mmoles/1 | % Red Color |
|---|---|---|
| None | — | 36 |
| CEPA | 0.248 | 63 |
| CEPA | 0.497 | 68 |
| NMP/CEPA 1:1 Molar Mixture | 0.270 | 70 |
| NMP/CEPA 1:1 Molar Mixture | 0.540 | 75 |

It was found that 1.03 mmoles/liter of Ethephon, i.e. CEPA, is required to produce 72% reddening of Cornell McIntosh apples in a similar treatment (see Table II of the paper published in The Journal of American Society for Horticultural Science, Volume 99, #3, Page 239, May 1974).

EXAMPLE XII

Apple Reddening

Three groups of 4 year old Millersturdeespur apple trees (5 in each group) were sprayed to run-off with the aqueous solutions noted in Table XVII. Another group of 5 four year old trees was left untreated as a control. After two weeks, the apples were harvested and physical measurements taken. The replicate results were averaged and reported as follows.

TABLE XVII

| Treatment | Rate mmoles/1 | % Red Color |
|---|---|---|
| None | — | 33 |
| CEPA | 0.248 | 38 |
| CEPA | 0.497 | 58 |
| NMP/CEPA 1:1 Molar Mixture | 0.270 | 65 |

EXAMPLE XIII

Walnut Loosening

Two groups of Ashley nut bearing walnut trees (5 trees in each group) were sprayed to run-off with the aqueous solutions noted in Table XVIII. Another group of 5 trees was left untreated as a control. After 10 days, the replicate results were averaged and reported as follows:

TABLE XVIII

| Treatment | Rate mmoles/Gal. | Leaf Fall | Harvestability % Removable |
|---|---|---|---|
| None | — | 0.0 | 50.0 |
| CEPA | 0.0145 | 3.0 | 99.5 |
| NMP/CEPA 1:1 Molar Mixture | 0.0078 | 1.2 | 86.0 |

Of the abscission ratings, 3 is considered excessive, 1 is considered slight and not harmful to the tree. The harvestability data in the above table was taken during normal harvest.

EXAMPLE XIV

Sour Cherry Loosening

Two groups of Montmorency fruit bearing sour cherry trees (3 trees in each group) had their branches sprayed to run-off with the aqueous solutions noted in Table XIX. Another group of 3 trees was left untreated as a control. After one week, replicate results were averaged and reported as follows. The fruit removal force measurements were made after seven days on a 100 fruit sample per replicate.

TABLE XIX

| Treatment | Rate mmoles/1 | Fruit Removal Force, Grams |
|---|---|---|
| None | — | 445 |
| CEPA | 1.375 | 281 |
| NMP/CEPA 1:1 Molar Mixture | 0.716 | 280 |

The above field test established that it requires about twice as much Ethephon, i.e. CEPA, to obtain a result approaching the present coacting mixture.

EXAMPLE XV

Filbert Loosening

Four groups of Barcellona nut bearing hazel trees (5 trees in each group) had their branches sprayed to run-off with the aqueous solutions noted in Table XX. Another group of 5 trees was left untreated as a control. After two weeks, the replicate results were averaged and reported as follows:

TABLE XX

| Treatment | Rate Moles/100 Gal. | % Drop |
|---|---|---|
| None | — | 14 |
| CEPA | 1.36 | 31 |
| CEPA | 2.61 | 43 |
| NMP/CEPA 1:1 Molar Mixture | 1.87 | 51 |
| NMP/CEPA 1:1 Molar Mixture | 2.82 | 55 |

EXAMPLE XVI

Grape Color Enhancement

Four groups of Zinfandel fruit bearing grape vines (5 vines in each group) were sprayed to run-off with the aqueous solutions noted in table XXI. Another group of 5 vines was left untreated as a control. The grapes harvested when the control brix was 22% after which the grapes were juiced to give solutions from which optical density measurements could be made. The replicate results were averged and reported as follows:

TABLE XXI

| Treatment | Rate mmoles/1 | % Color |
|---|---|---|
| None | — | 50 |
| CEPA | 3.93 | 90 |
| NMP/CEPA 1:1 Molar Mixture | 2.45 | 100 |
| NMP/CEPA 1:1 Molar Mixture | 0.67 | 70 |
| NMP/CEPA 1:1 Molar Mixture | 0.09 | 40 |

It was also found that the grapes treated with the present mixture ripened at least 4 days sooner than those treated with ethephon (CEPA) thus permitting earlier harvest and insurance against rain damage in postharvest treatment.

EXAMPLE XVIII

Sex Expression of Cucumbers

Two groups of Galaxy cucumbers (2 plants in each group) were sprayed to run-off after the first true leaf stage with the aqueous solutions noted in Table XXII. Another group of 2 plants was left untreated as a control. The replicate results were averaged and reported as follows.

TABLE XXII

| Treament | Rate mmoles/1 | Male/Female Flower Ratio | Internode Distance* Centimeters |
|---|---|---|---|
| None | — | 38.6 | 144 |
| CEPA | 0.0412 | 8.8 | 131 |
| CEPA | 0.1237 | 4.1 | 123 |
| NMP/CEPA 1:1 Molar Mixture | 0.0445 | 3.4 | 118 |
| NMP/CEPA 1:1 Molar Mixture | 0.1336 | 1.3 | 100 |

*Total distance of 1–15 internodes.

EXAMPLE XVIII

The degree to which the present coacting mixtures are capable of effecting ethylene generation was determined as follows:

In a growth chamber maintained at 30° C. and 2,000 to 3,000 foot candle light, soybean plants from the same seed source were grown to the unifoliate stage of development. Each of the following experiments were carried out in quadruplicate, and the results (found to be highly reproducible) were averaged and reported in following Table XXIII.

In each of the experiments, sixteen leaf disc samples from the unifoliate plant sources were removed by cutting the leaf with a circular cork borer of 1.78 cm diameter. Each of the sixteen leaf discs were then floated for 30 minutes in a closed Petri dish on 25 ml of water as a control or with 25 ml of aqueous solutions containing either 1,000 ppm (Low Rate) or 3,000 ppm (High Rate) of the equimolar mixture of cyclic monoamide/CEPA or polyvinylpyrrolidone/CEPA to be tested. At the end of 30 minutes, the leaf discs were removed from the solution, patted dry, and four each were reinserted in 4 10 ml vials fitted with a septum through which a syringe could be inserted for extracting a sample of the supernatant atmosphere. Four replicate gas samples for each compound were taken after the samples were allowed to stand in the light for one hour. The samples were analyzed for ethylene content by gas liquid phase chromatography. The vials were then placed in the dark for fifteen hours after which the gas above the leaf discs was resampled and analyzed in the manner similar to that described. The results, based the amount of deviation from an untreated control, are reported in Table XXIII in nanoliters of ethylene per liter of atmosphere per cm² of leaf surface per mole of test mixture and are based on the average of four replicate samples.

TABLE XXIII

| AMIDE COMBINED WITH CEPA (1:1) | Rate | nl Ethylene/ liter/cm²/mmole 1 hr (a) | 15 hr (b) |
|---|---|---|---|
| N—methyl-2-pyrrolidone | Low | 6,720 | 21,904 |
|  | High | 6,690 | 17,496 |
| Pyrrolidone | Low | 4,202 | 16,919 |

TABLE XXIII-continued

| AMIDE COMBINED WITH CEPA (1:1) | Rate | nl Ethylene/ liter/cm$^2$/mmole 1 hr (a) | 15 hr (b) |
|---|---|---|---|
| N—methyl-2-pyridone | High | 2,859 | 13,863 |
|  | Low | 4,368 | 15,647 |
| N—methyl-2-piperidone | High | 4,991 | 14,681 |
|  | Low | 4,282 | 11,850 |
| N—(O—tolyl)pyrrolidone | High | 4,603 | 18,988 |
|  | Low | 3,379 | 15,311 |
| N—(2-hydroxyethyl)-pyrrolidone | High | 6,912 | 15,268 |
|  | Low | 3,563 | 16,654 |
| N—isopropyl-2-pyrrolidone | High | 4,412 | 15,295 |
|  | Low | 3,743 | 15,090 |
| Polyvinyl-2-pyrrolidone (K30) | High | 4,805 | 14,264 |
|  | Low | 4,679 | 18,726 |
| 2-Chloroethylphosphonic acid | High | 5,223 | 16,689 |
|  | Low | 4,912 | 15,944 |
|  | High | 4,876 | 14,034 |

Unifoliate Plants
a. in light
b. in dark
c. untreated tissue (control) gave 125 nl ethylene/liter/cm$^2$ after 1 hour and 180 nl ethylene/liter/cm$^1$ after 16 hours.
Low = 1,000 ppm
High = 3,000 ppm

EXAMPLE XIX

Twenty peach trees of the Redglobe variety were sprayed after fruit set with an aqueous 150 ppm solution of NMP/Ethephon mixture in a 1:1.2 mole ratio at a rate of 200 gallons per acre. The weather conditions at the time of spraying were: temperature at 82° F.; humidity 67%; cloudy, mild Easterly wind at 5 mph.

Another 20 peach trees of the same variety at the same stage of development and growing under substantially the same conditions were left unsprayed as a control.

Five days after spraying the treated trees began to drop their fruit and within 8 days almost complete fruit drop had occurred; only 4 to 5 peaches remained on each tree. The abscission was selective to fruit so that almost no leaf defoliation occurred. In contrast, the untreated trees remained heavily laden with fruit. Any of the fruit trees bearing apples, pears, oranges, lemons, plums, grapefruit or apricots, can be substituted in this example with similar effect.

The above results establish that the present mixture is a highly effective chemical thinning agent and a harvesting aid when applied at the outset of fruit ripening in concentrations between about 50 and about 200 ppm.

EXAMPLE XX

The present mixture 1:2 mole ratio of NMP/Ethephon at a concentration of 1500 ppm in aqueous solution containing 0.3% of a thickening agent, (guar gum) to form a syrupy paste when applied in a band around the trunk of a sugar maple below the tapping site, significantly increases sap flow to provide a sustained yield increase of at least 15% without deleterious effect to the tree. This effect is also induced in rubber trees. It is theorized that the present mixture exerts an anticoagulant effect on the sap when exposed to air and increases the flow of sap or latex.

EXAMPLE XXI

The present 1:3 mole ratio mixture of NMP and ethephon when applied to the graminae family of plants, eg. wheat, rye, oats, corn and rice, in a concentration of 200 ppm, except in the case of cotton which was treated at 1,000 ppm, in aqueous solution, induces the formation of shorter plants. The above effect is also obtained when tomato plants are substituted in this example. The height of corn, wheat, rice, rye, barley and oats is reduced by at least 25% so that lodging is eliminated with a low dosage level of chemical.

EXAMPLES XXII–XXXV

Tobacco Ripening

The following experiments were conducted to determine the efficacy of the present mixture as a ripening agent for flue-cured tobacco and to compare the rate of ripening (leaf yellowing) and quality of flue cured tobacco of the mixture with that of ethephon.

Four 40 feet rows of about 100 Speight tobacco plants growing in Florida were treated with a $CO_2$ charged sprayer delivering 40 gallons/acre of an aqueous solution (0.0069 lb. mole/acre) of a 1:1 molar mixture of N-methylpyrrolidone and 2-chloroethylphosphonic acid. A similar size plot was identically sprayed with an aqueous solution of ethephon (0.0069 lb mole/acre) and a third plot of the same size was left untreated as a control. Two additional plots of the same size having the same number of tobacco plants were similarly sprayed with said 1:1 molar mixture and with ethephon, except that a rate of 0.0138 lb mole/acre was employed. The temperature at the time of treatment ranged from 72° F. night to 94° F. day temperature. Yield determinations were made by harvesting all plots at the same time (4 days after treatment for sprayed plots) and curing the harvested leaves in a curing barn. The results are reported in the following Table XXIII.

TABLE XXIII

| Example No. | Treating Agent | Rate lb. mole/ Acre | Yield lb/Plot | Quality Grade |
|---|---|---|---|---|
| XXII | Control | — | 6.55 | Choice-Medium bodied-green |
| XXIII | NMP/Ethephon Mix | 0.0069 | 5.77 | Choice-Varigated greenish orange |
| XXIV | Ethephon | 0.0069 | 5.00 | Choice-Varigated but most green with flecks of orange |
| XXV | NMP/Ethephon Mix | 0.0138 | 3.86 | Choice-Varigated greenish orange |
| XXVI | Ethephon | 0.0138 | 4.36 | Choice-Varigated greenish orange |

In these experiments, a reduced yield is expected since plant growth regulators generally have this effect due to earlier ripening. However, it is shown that the present mixture has a minimal influence on yield (significantly less than Ethephon at the lower dosage rate).

The present mixture at 0.0069 lb mole/acre not only ripened the tobacco at a rate equivalent to the 0.0138 lb mole rate of Ethephon but also provided tobacco of superior quality at the lower level. Equivalent quality was achieved with ethephon alone only at the higher level.

The procedure outlined above was repeated on plots in North Carolina to compare the quality and ripeness promotion of leaf tobacco, results of which are reported in the following Table XXIV. The quality was rated on a scale of 1-6, with 1 being choice and 6 being poor.

TABLE XXIV

| Example No. | Treating Agent | Rate lb. mole/ Acre | Days to Harvest After Treatment | Grade/Color |
|---|---|---|---|---|
| XXVII | Control | — | 14 | 3-4/Varig. orange to lemon |
| XXVIII | NMP/Ethephon 1:1 Molar | 0.0035 | 5 | 3-4/Varig. orange |
| XXIX | Ethephon | 0.0069 | 4 | 4/Varig. orange |
| XXX | NMP/Ethephon 1:1 Molar | 0.0069 | 3 | 3-4/Varig. orange |
| XXXI | Ethephon | 0.0138 | 3 | 4-5/Varig. orange |

The treatment at 0.0035 lb. mole/acre with 1:1 molar NMP/Ethephon achieved the same yield of high quality crop as the control and days to harvest were significantly reduced. Plots grown in South Carolina were similarly treated to study hastening of ripening. The results of these tests are given in Table XXV.

TABLE XXV

| Example No. | Treating Agent | Rate lb. Mole/ Acre | Days to Harvest | Quality |
|---|---|---|---|---|
| XXXII | Control | — | 21 | 3 |
| XXXIII | NMP/Ethephon (1:1 Molar) | 0.0069 | 4 | 3 |
| XXXIV | Ethephon | 0.0069 | 16 | 3 |
| XXXV | Ethephon | 0.0138 | 4 | 3 |

HERBICIDAL ACTIVITY OF MIXTURE

EXAMPLES XXXVI THROUGH XXXVIII

Honey mesquite seedlings were grown from seeds in a 1:1:1 mixture of sand, peat and clay loam soil in a greenhouse. Ten week old seedlings were then sprayed to run off with an aqueous solution of NMP/Ethephon, (1:1 mole ratio) mixture. The treating solution also contained polyethylated sorbitol monolaurate surfactant (Oxysorbic) at a 0.1% concentration.

The above spraying process was repeated except that Ethephon was substituted for the NMP/Ethephon mixture. Each treatment was replicated with 80 seedlings. Another group of 10-week old seedlings were left untreated as a control. The results of these treatment are shown in the following Table XXVI.

TABLE XXVI

| Example No. | Agent | Concentration g/l(mole/l) | % Contact Injury | Branches per plant | % Stem # Mortality |
|---|---|---|---|---|---|
| XXXVI | Control | 0 | 4.0[b] | 0 | 0 |
| XXXVIIA | NMP/Ethephon Mixture | 15(0.061) | 95.1 | 1.7 | 3.0 |
| XXXVIIIA | Ethephon | 15(0.103) | 90.3 | 1.1 | 1.6 |
| XXXVIIB | NMP/Ethephon Mixture | 45(0.184) | — | — | 98.9 |
| XXXVIIIB | Ethephon | 45(0.310) | — | — | 97.5 |

[b]Contact injury rated 1 week after treatment, all other parameters measured 3 weeks after treatment. Stem mortality and contact injury are rated on a scale of 0% (no effect) to 100% (complete defoliation or mortality).

As shown above, the dosage of ethephon can be reduced by half through the coaction of the N-heterocyclic amide and achieve improved herbicidal effects.

After making the above observations, the histology of the mixture treated tissues was studied by collecting specimens from positions all along the stem of the mixture treated group of plants. These were fixed in a solution of glutaraldehydeparaformaldehyde, sectioned traversely on a sliding microtome with a freezing attachment and stained. It was observed that aberrant phloem development had taken place, groups of axial parenchyma cells became massively hypertrophied, underwent proliferation and gave rise to gum pockets at both nodal and internodal positions. In some cases the pockets formed a discontinuous tangential ring in the phloem all around the stem axis. Gum was often seen as clear droplets or ribbons extruding from the epidermal stem surface through schizogenously developed canals in the cortex by rupture of the epidermal layer. The treating agents produced little or no cortex proliferation and both induced branching without affecting apices.

EXAMPLES XXXVIX THROUGH XLIII

Huische seedlings were grown from seeds in a 1:1:1 mixture of sand, peat and clay loam soil in a greenhouse. Ten week old seedlings were then sprayed to run off with aqueous solutions of NMP/Ethephon, in a 1:1 mole ratio, containing 0.1% polyethylated sorbitol monolaurate surfactant. The spraying operation was repeated except that Ethephon was substituted for the NMP/Ethephon mixture. Each treatment was replicated with 80 seedlings. Another 80 seedling group of plants was left untreated as a control.

The results of the treatments after 20 days are shown in following Table XXVII.

TABLE XXVII

| Example No. | Agent | Concentration g/l(mole/l) | % Stem Mortality |
|---|---|---|---|
| XXXIX | Control | 0 | 0 |
| XL | NMP/Ethephon | 15 (0.061) | 26 |
| XLI | Ethephon | 15 (0.103) | 18 |
| XLII | NMP/Ethephon | 45 (0.184) | 88% |
| XLIII | Ethephon | 45 (0.310) | 26% |

The present mixture at 15 g/liter (0.061 moles/liter) achieves the same % stem mortality as Ethephon at 45 g/liter (0.310 moles/liter). The mixture also showed better penetration than ethephon and promoted radial expansion and cortex proliferation on the stems but caused no gummosis. Substitution of 2-bromoethylphosphonic acid for ethephon in Examples XXXVII, XL and XLII in admixture with NMP provides substantially the same results.

Although Ethephon induces shorter internode response in plants, the detrimental side effects of this plant growth regulant for plants of the Graminae family have prevented its wide acceptance. Specifically, Ethephon inhibits flowering, seedheads are malformed or underdeveloped and about 50% are aborted after treatment. Consequently, certain grass seeds treated with as little as 1 or 2 Kg/ha lack the ability to germinate. Other undesirable side effects resulting from the treatment with this chemical include shoot-tip dieback, browning or chlorosis of foliage, and interruption of rhizome development. When a portion of ethephon is replaced with an amount of the present N-heterocyclic amides, preferably to provide a ratio of between about 0.15:1 and about 3:1 NMP/Ethephon, the deleterious side effects are minimized or eliminated while the internodal stem segments are appreciably reduced. These advantageous results are obtained in the treatment of rye grass, bent grasses, Bermuda grass, Kentucky bluegrass, fescue and other turf grasses in which the stem elongation growth rate is reduced by 10–40%, and shorter plants of a more branched and/or rhizomed structure than normally obtained are developed, while maintaining the plant's ability to propagate either through rhizome generation or seed germination. An additional advantage is realized in that the present mixture can be applied to fully-matured plants without the harmful effects discussed above. While several plant growth regulants have been effectively employed to slow the growth of seedling turf grasses, they are not practical for application over an extended period since they exhibit a herbicidal effect on established, fully-matured plants. Beneficial mixtures for use on grasses include Ethephon/polyvinyl-2-pyrrolidone** in a mole ratio of from about 4:1 to about 10:1, Ethephon/N-methyl-2-pyrrolidone in a mole ratio of between about 1:2 and about 2:1; Ethephon/2-pyrrolidone in a mole ratio of about 1.5:1 to 2:1; Ethephon/mixture of N-methyl-2-pyrrolidone (1 part) and polyvinyl-2-pyrrolidone-K 30* (1 part) in a mole ratio of between about 1:1 and about 4:1; although it is to be understood that other mixtures discussed in the foregoing disclosure can also be employed for the treatment of Gramineae to obtain the abovediscussed benefits.

*225–250 vinyl-2-pyrrolidone units
**about 800–1,200 vinyl-2-pyrrolidone units

While claims have been made for increasing the yield of cereal grasses by treatment with Ethephon, it should be understood that this increase is based on shorter internodal growth and decreased unrecoverable crop due to lodging. There is substantially no increase in the size of the grain or grainheads, while epinasty, seed malformation and seedhead abscission are ever-present problems. Treatment with the present coacting admixtures overcomes these difficulties while still retaining the desirable results. The following examples illustrate the beneficial effects of certain preferred admixtures.

EXAMPLES XLIV THROUGH LXI

Separate 50-plant plots, containing rye grass, Johnson grass, zoysia, and winter wheat, all at the tillering stage, sprayed to run off with 4–5 Kg/ha of the aqueous solutions noted in Examples XLIV–XLVIII and L–LXI below in table XXVIII, result in significant decrease in the average rate of stem elogation 3 months after treatment. The mixture-treated plants achieve 100% normal rhizome development and are free of phytotoxic effects, such as chlorosis and blanching. The absence of shoot-tip dieback and abortion or malformation of grass seedheads are also beneficial effects achieved with the present mixtures.

TABLE XXVIII

| Example No. | Plant Height Inhibitor | Rate of Appln. Kg/ha | 3 Months after Spraying | | 5 Days after Spraying % Chlorosis |
|---|---|---|---|---|---|
| | | | Av. Rate Decrease in Stem Elong. (cm/week) | % Seadhead Malformed or Aborted | |
| | | RYE GRASS | | | |
| XLIV | Ethephon | 4 | 1.5 | 15 | 10 |
| XLV | Ethephon/NMP (2:1 mol. mix.) | 4 | 2 | 2 | 0 |
| LXVI | Ethephon/PVP-K30 (4:1 mol. mix.) | 4.5 | 1.3 | 2 | 0 |
| XLVII | Ethephon/2-pyrrolidone (1:1 mol. mix) | 5 | 2 | 4 | 2 |
| XLVIII | Ethephon/NMP (1:3 mol. mix) | 4 | 1.0 | 2 | 0 |
| LXIX | Untreated | — | — | 2 | 0 |
| | | JOHNSON GRASS | | | |
| L | Ethephon | 4 | 2.5 | 70 | 5 |
| LI | Ethephon/NMP (2:1 mol. mix.) | 4 | 2.8 | 25 | 0 |
| LII | Ethephon/PVP-K60 (1:1 mol. mix.) | 4.5 | 2.6 | 15 | 0 |
| LIII | Ethephon/NMP (1:3 mol. mix.) | 4 | 2.2 | 2 | 0 |
| | | ZOYSIA | | | |
| LIV | Ethephon/NMP (2:1 mol. mix.) | 4 | 1.5 | 0 | 0 |
| LV | Ethephon/NMP (1:1 mol. mix.) | 4 | 1.8 | 0 | 0 |
| LVI | Ethephon/NMP (1:3 mol. mix.) | 4 | 0.8 | 0 | 0 |
| LVII | Ethephon | 4 | 1.0 | 15 | 10 |
| | | WINTER WHEAT | | | |
| LVIII | Ethephon/NMP (2:1 mol mix) | 4 | 1.5 | 0 | 0 |
| LVIX | Ethephon/NMP (1:1 mol. mix.) | 4 | 1.9 | 0 | 0 |
| LVX | Ethephon/NMP (1:3 mol. mix.) | 4 | 0.6 | 0 | 0 |

TABLE XXVIII-continued

| Example No. | Plant Height Inhibitor | Rate of Appln. Kg/ha | 3 Months after Spraying | | 5 Days after Spraying % Chlorosis |
|---|---|---|---|---|---|
| | | | Av. Rate Decrease in Stem Elong. (cm/week) | % Seadhead Malformed or Aborted | |
| LXI | Ethephon | 4 | 0.8 | 25 | 5 |

PVP = polyvinylpyrrolidone;
NMP = N—methyl-2-pyrrolidone

Examples LVIII to LVX on Winter Wheat also provide a greater number of grain flowers per spikelet so that crop yield may be increased by about 10–20%.

Generally, it is noted above that the rate of stunting is diminished as the amount of NMP is increased above about a 2 molar excess NMP with respect to Ethephon; although significant reduction in normal stem elongation over longer periods is obtained at even higher excesses of NMP.

EXAMPLE LXII

An aqueous solution containing a mixture of 600 ppm 2-bromoethylphosphonic acid and 200 ppm N-methyl-2-pyrrolidone is sprayed to run off on one half a plot of ryegrass which had been cut back to a height of 1.5 inches and, after one week, compared to ryegrass in the remaining half untreated section of ryegrass cut to similar height. The height of the grass in the treated section measured only 1.75 inches; whereas in the untreated section, normal growth produced 2.5 inch tall plants.

The retarded rate of growth in the height of plants is repeated on Kentucky bluegrass, fescue, Bermuda grass and other turf grasses as well as cereal grasses such as for example, the grasses including oats, wheat, barley, rice, corn, etc. when the above treatment is employed. Also, in these treatments to slow the rate of growth in plant height, 2-chloroethylphosphonic acid can be substituted above for the 2-bromoethylphosphonic acid and 2-pyrrolidone, N-methyl-2-pyridone, or polyvinyl pyrrolidone, or amide mixtures thereof can be substituted for the N-methyl-2-pyrrolidone above and employed in a mole ratio of between 0.75:1 and 6:1 (acid to amide) at a concentration in carrier of from about 500 ppm to 1,500 ppm to provide substantially the same growth response.

EXAMPLES LXIII THROUGH LXIX

Promotion of Seed Germination

Eight groups of 20 sunflower seeds from the same seed source are separately immersed for 1.5 hours in separate aqueous solutions each containing 500 ppm of a different plant growth regulating agent as defined in Table XXIX. An additional water solution containing no plant growth regulating agent is provided as a control in which 20 additional seeds are immersed for the same period. The number of seeds germinated for each treatment 5 days after immersion, being planted in flats and exposed to standard light and humidity conditions in a greenhouse, is shown below.

TABLE XXIX

| Example No. | Active Regulant | Seed Germination % |
|---|---|---|
| LXIII | Control | 4 |
| LXIV | Ethephon | 6 |
| LXV | Ethephon/N—methyl-2-pyrrolidone (1:1 molar mixture) | 9 |
| LXVI | Ethephon/N—methyl-2-pyrrolidone (1:1.5 molar mixture) | 8 |
| LXVII | Ethephon/PVP Tetramer (10:1 molar mixture) | 7 |
| LXVIII | Ethephon/PVP Tetramer (3:1 molar mixture) | 8 |
| *LXIX | Ethephon/N—methyl-2-pyrrolidone (1:1 molar mixture) | 9 |

*Seeds immersed in water for 1.5 hours and then planted in soil predrenched with the aqueous solution of Example LXV.

As the time from planting is extended to 10 days, the number of seeds germinated is increased; however, the proportional differences among the regulating agents are generally maintained.

Many types of weeds, such as for example pigweed, witchweed, bindweed, Johnson grass, cocklebur, nutsedge, Kochia, nightshade, etc. produce seeds capable of germination over an extended period, e.g. several years. Accordingly, seasonal protection against such weeds has not been feasible unless repeated doses of herbicide or objectionable herbicides, of high toxicity or long residual life, have been employed.

According to this invention, it is desirable to promote and standardize the time of seed germination in order that all seeds germinate at about the same time and a short residual herbicide can be applied to clear an area of unwanted weeds for a significantly prolonged period. The following example illustrates this desired effect.

EXAMPLE LXX

Three replicates consisting of 50 witchweed seeds each, deposited on filter paper saturated with 0.0001 ppm of a 1:1 molar mixture of NMP/Ethephon in aqueous solution are allowed to soak in petri dishes for 6 hours, before planting in sterilized soil. The percent of seed germination obtained from the treated seeds within a 3 week period is increased 80 times the normal germination (1%) within the same period and is equivalent to the % of seed germination obtainable with Strigol, a natural germination stimulant extracted from the leaves of the witchweed plant.

When the above treatment is repeated on cotton seeds, a similar increase in seed germination is obtained after planting; thus indicating the importance of the present mixture for seed crops, to effect, not only increased seedling emergence, but also as a means of synchronizing crop development for single crop harvest.

It is to be understood that alternate methods of contacting seeds with the mixtures of the present invention may also be employed. For example, the soil in a specified area may be drenched, sprayed or dusted with the present mixtures and the seeds planted shortly (e.g. several hours to one day) after the soil preparation.

These and many more methods of contacting will become apparent to those familiar with agricultural treating methods.

EXAMPLES LXXI THROUGH LXXV

Four groups of fruit bearing sweet Bing cherry trees (3 trees in each group) were sprayed to run-off with the aqueous solutions noted in Table XXX. Another group of 3 Bing cherry trees was left untreated as a control. Replicate results were averaged and reported 5–16 days after spraying. The fruit removal force measurements were made on a 100 fruit sampling per replicate. Additionally, grams of soluble solids and % sugars were determined by refractometer readings of the extracts of pressing liquor. Treatment with the present mixture provided essentially the same fruit sweetness and firmness as the control or other treating agents while minimizing the pull force needed for fruit harvest.

TABLE XXX

| Example No. | Treatment | Fruit Removal Force (gms) Days After Spraying (Harvest) | | | | Soluble Solids Days After Spraying (Harvest) | | | |
|---|---|---|---|---|---|---|---|---|---|
| | | 5 | 9* | 13 | 16 | 5 | 9* | 13 | 17 |
| LXXI | Control | 687 | 610 | 624 | 605 | 20.0 | 21.9 | 22.5 | 24.1 |
| LXXII | Ethephon 200 ppm + GA 15 ppm (1) | 607 | 428 | 413 | 315 | 20.6 | 23.1 | 24.0 | 24.7 |
| LXXIII | Ethephon 200 ppm | 571 | 419 | 337 | 429 | 20.4 | 21.1 | 22.9 | 22.6 |
| LXXIV | CGA 200 ppm (2) | 491 | 408 | 368 | 408 | 22.4 | 22.0 | 23.8 | 24.6 |
| LXXV | Ethephone 118 ppm + NMP 82 ppm | 548 | 402 | 307 | 361 | 20.2 | 19.7 | 21.9 | 22.9 |

PPM were determined by percent active ingredient on a weight basis
*Optimum harvest date.
(1) GA = gibberellic acid
(2) CGA = 2-chloroethyl-methyl-bis(benzyloxy) silane

EXAMPLES LXXVI THROUGH XC

Sweet Bing cherries (100 from each of the above treatments on the thirteenth day after spraying) were harvested and 10 from each group were stored at a different temperature for 1 month, i.e. 10 at 28° F., 10 at 30° F. and 10 at 32° F. Another 10 cherries from each group were stored at the same temperatures for 1 month and were then held an additional 5 days at 65° F. Still another 10 cherries from each group were stored at the same temperatures for 1 month and were then held an additional 10 days at 65° F. At the end of these respective periods, the cherries were evaluated for % of unrotted sound fruit and fruit firmness measured by a penetrometer in grams of force needed to burst the skin. The tests indicated the effects of the various chemical agents on the harvested crop. The results of these tests were averaged and reported in following Table XXXI.

TABLE XXXI

| Example No. | Treatment | Pull Force (grams) | Sound Fruit (%) Storage Temp. F. | | | Fruit Firmness (grams) Storage Temp. F. | | |
|---|---|---|---|---|---|---|---|---|
| | | | 28° | 30° | 32° | 28° | 30° | 32° |
| | Stored 1 month | | | | | | | |
| LXXVI | Check | 624 | 80 | 75 | 74 | 125 | 125 | 122 |
| LXXVII | CGA - 200 ppm | 368 | 73 | 72 | 66 | 127 | 126 | 126 |
| LXXVIII | Ethephon - 200 ppm | 337 | 69 | 71 | 69 | 126 | 124 | 124 |
| LXXIX | Ethephon - 200 ppm + GA - 15 ppm | 413 | 70 | 65 | 62 | 131 | 130 | 129 |
| LXXX | Ethephon - 118 ppm + NMP - 82 ppm | 307 | 64 | 61 | 66 | 126 | 124 | 124 |
| | Stored 1 month plus 5 days at 65° | | | | | | | |
| LXXXI | Check | 624 | 56 | 57 | 32 | 124 | 124 | 122 |
| LXXXII | CGA - 200 ppm | 368 | 62 | 54 | 32 | 124 | 128 | 123 |
| LXXXIII | Ethephon - 200 ppm | 337 | 50 | 58 | 34 | 120 | 122 | 120 |
| LXXXIV | Ethephon - 200 ppm + GA - 15 ppm | 413 | 58 | 44 | 28 | 127 | 129 | 128 |
| LXXXV | Ethephon - 118 ppm + NMP - 82 ppm | 307 | 38 | 39 | 24 | 119 | 120 | 119 |
| | Stored 1 month plus 10 days at 65° | | | | | | | |
| LXXXVI | Check | 624 | 45 | 44 | 43 | — | — | — |
| LXXXVII | CGA - 200 ppm | 368 | 44 | 38 | 28 | — | — | — |
| LXXXVIII | Ethephon - 200 ppm | 337 | 38 | 32 | 30 | — | — | — |
| LXXXIX | Ethephon - 200 ppm + GA - 15 ppm | 413 | 19 | 23 | 15 | — | — | — |
| XC | Ethephon - 118 ppm + NMP - 82 ppm | 307 | 12 | 20 | 21 | — | — | — |

EXAMPLES XCI THROUGH XCV

Another four groups of Bing sweet cherry trees (3 in each group) were sprayed to run-off with 200 ppm of the above treating agents in aqueous solution as noted in the following table, and a fifth group of three was left untreated as a control. After harvesting the fruit and 25 days after spraying, the tree trunks were inspected for gumming sites. A small amount of gummosis occurs naturally as a result of senescensce after fruit harvest; however, this effect should be kept to a minimum so as to prevent permanent damage to the tree, e.g., shortening fruit bearing life, reducing crop quality and quantity in future fruiting and lowering resistance to disease. The results of these tests were averaged and reported in following Table XXXII, wherein it is shown that the present/mixture of Ethephon and NMP significantly reduced tree trunk gummosis over the other chemicals tested.

TABLE XXXII

| Example No. | Treatment | Tree Number | No. of Sites on Tree Trunk |
|---|---|---|---|
| XCI | Control | 1-1 | 0 |
|  |  | 2-5 | 1 |
|  |  | 2-6 | 0 |
|  |  | Average | 0.3 |
| XCII | CGA - 200 ppm | 1-2 | 1 |
|  |  | 2-2 | 4 |
|  |  | 1-3 | 2 |
|  |  | Average | 2.3 |
| XCIII | Ethephon - 118 ppm + NMP - 82 ppm | 1-4 | 1 |
|  |  | 2-3 | 2 |
|  |  | 1-6 | 1 |
|  |  | Average | 1.3 |
| XCIV | Ethephon - 200 ppm | 2-1 | 0 |
|  |  | 1-5 | 3 |
|  |  | 2-4 | 2 |
|  |  | Average | 1.6 |
| XCV | Ethephon - 200 ppm + GA - 15 ppm | 1-8 | 5 |
|  |  | 1-9 | 4 |
|  |  | 1-10 | 1 |
|  |  | Average | 3.3 | results in deterioration of quality and incidence of damage by diseases or pests, e.g., the naval orange worm. Accordingly, it is most desirable to induce hull dehiscence and nut removal as soon as possible after determining kernel maturity and nut drop.

The present study was conducted to (1) test the efficacy of the above solutions for inducing hull dehiscence, (2) determine the quality of the treated nuts and (3) to assess the return crop in the following year. Each treatment was replicated 5 times and was applied by spraying to run off about 7 days after the packing tissue between the kernels had browned (i.e., the PGB stage). The treated tree crop was harvested with a single pole shake and nut samples of 36 to 80 nuts randomly taken from each tree were hulled, dried, and evaluated for quality. In the following year, these trees were rated for return crop and fruit set. No diminution of crop or crop quality was observed.

In the case of the control, repeated thrashing was necessary for the removal of sufficient nuts for sampling. The averaged results of these tests are reported in Table XXXIII, which follows:

TABLE XXXIII

| Example No. | Treatment PPM | Hullability % | Adhering Hulls % | KERNEL QUALITY | | | | INTERNAL DAMAGE | | | EXTERNAL DAMAGE | Off Grade % |
|---|---|---|---|---|---|---|---|---|---|---|---|---|
|  |  |  |  | % Light | % Light Amber | % Amber | Total Amber (Edible) | Mold % | Insect % | Shrivel % | (1) % |  |
| NORTHERN DISTRICT |  |  |  |  |  |  |  |  |  |  |  |  |
| XCVI | Control | 23 | 12 | 28.4 | 2.6 | 1.8 | 32.8 | 0.44 | 17.54 | 12.28 | 0 | 7.0 |
| XCVII | 100 NMP- 150 Ethephon | 62 | 5 | 34.6 | 2.8 | 5.0 | 40.4 | 0 | 8.12 | 5.13 | 1.71 | 3.0 |
| XCVIII | 210 NMP- 290 Ethephon | 68 | 2 | 33.4 | 3.6 | 1.6 | 39.4 | 0.83 | 8.30 | 4.98 | 2.06 | 3.8 |
| XCVIX | 315 NMP- 435 Ethephon | 92 | 1 | 33.0 | 5.4 | 2.0 | 40.4 | 0 | 5.02 | 6.28 | 2.09 | 2.4 |
| C | 500 Ethephon | 92 | 1 | 31.2 | 6.8 | 1.6 | 39.6 | 0 | 7.14 | 6.70 | 1.44 | 3.4 |
| SOUTHERN DISTRICT |  |  |  |  |  |  |  |  |  |  |  |  |
| CI | Control | 90 | — | 30.0 | 10.4 | 4.6 | 45.0 | — | — | — | — | 4.0 |
| CII | 100 NMP- 150 Ethephon | 98 | — | 35.8 | 6.4 | 2.4 | 44.6 | — | — | — | — | 5.2 |
| CIII | 210 NMP- 290 Ethephon | 100 | — | 32.6 | 9.6 | 2.0 | 44.2 | — | — | — | — | 5.2 |
| CIV | 315 NMP- 435 Ethephon | 100 | — | 16.0 | 19.6 | 5.4 | 41.6 | — | — | — | — | 5.2 |
| CV | 500 Ethephon | 100 | — | 28.2 | 14.4 | 1.6 | 44.2 | — | — | — | — | 4.8 |

(1) Splitting, perforation and/or staining

EXAMPLES XCVI THROUGH CV

The mixtures of this invention were also found to be superior dehiscence aids in hulling nuts. Twenty-five Ashley walnut trees from the northern and southern districts of California, of similar size, leaf and crop area were selected for treatment. Five aqueous treating solutions were made up for comparative testing. The first solution consisted of water and was used as a control; the second solution contained 150 ppm Ethephon and 100 ppm NMP; the third solution contained 290 ppm Ethephon and 210 ppm NMP; the fourth solution contained 435 ppm Ethephon and 315 ppm NMP; and the fifth solution contained 500 ppm Ethephon.

Walnuts are generally harvested by mechanically shaking the trees when at least 80% of the nuts can be removed and edible kernels are mature and of highest quality, i.e., the packing tissue between the kernels and the shell has darkened to an amber or brown color. This harvesting is generally effected before hulling dehiscence. Delay in harvesting the mature kernels often The above testing results show the promotion Ethephon activity with NMP, such that substantially less Ethephon (435 ppm in Examples XCVIX and CIV) achieve similar results as 500 ppm Ethephon in hull dehiscence. Proportionately, a significantly greater number of walnuts matured to the edible amber stage when treated with the present mixture containing 315 ppm NMP and only 435 ppm Ethephon and slightly better quality kernels is observed with only 150 ppm Ethephon promoted with 100 ppm NMP.

Similar advancement of percent hullability is achieved when treating other nut crops, e.g., peanuts, filberts, almonds, chestnuts, hickory nuts, pistachios, brazil nuts, peacans, cashews, macadamia, etc. with the mixtures reported in the Table XXXIII and other mixtures within the scope of this invention.

In the above examples illustrating representative mixtures, of this invention, it is to be understood that any of the other haloalkyl phosphonic acids such as for example the fluorinated, chlorinated, brominated or iodonated ethyl phosphonic acids, their corresponding anhydrides or corresponding catechol esters can be substituted to produce similar plant growth regulating effects and benefits.

Also, any of the monoamides or monoamide polymers included within the scope of this invention, such as e.g. N-ethyl-2-pyrrolidone, N-methyl-2-pyrrolidone, 2-pyrrolidone, N-ethyl-2-pyridone, N-methyl-2-pyridone, N-propyl-2-pyridone, 2-pyrrolone, N-methyl-2-pyrrolone, N,N'-dimethylantipyrine, N-methyl-2-piperidone, N-ethyl-2-piperidone, 2-piperidone, N-hydroxyethyl-2-pyrrolidone, N-isopropyl-2-pyrrolidone, N-phenyl-2-pyrrolidone, N-(o-tolyl)-2-pyrrolidone, polyvinyl pyrrolidone of between about 20,000 and about 550,000 number average molecular weight, as well as lower molecular weight polymers, e.g., vinyl-2-pyrrolidone dimer, trimer tetramer, etc. can be substituted in any of the foregoing examples to provide compounds having similar utility on plants herein described.

We claim:

1. A plant growth regulating composition consisting essentially of an ethylene-generating amount of a 2-haloethylphosphonic acid selected from the group consisting of 2-haloethylphosphonic acid, 2-haloethylphosphonic acid anhydride and 2-haloethylphosphonic catechol ester and mixtures thereof, and a N-heterocyclic amide selected from the group consisting of N-methylpyrrolidone, polyvinylpyrrolidone, pyrrolidone, and N-methylpiperidone in an amount sufficient to promote the ethylene-generating, plant growth regulating effect of said 2-haloethylphosphonic acid compound.

2. A plant growth regulating composition of claim 1 wherein said haloethylphosphonic compound is 2-haloethylphosphonic acid.

3. The plant growth regulating composition of claim 2 wherein the mole ratio of said N-heterocyclic amide to said 2-haloethylphosphonic acid is between about 0.005:1 and about 15:1.

4. The plant growth regulating composition of claim 3 wherein said composition is dissolved in an inert carrier and the concentration of said mixture in said inert carrier is between about 0.00001 ppm and about 100,000 ppm.

5. The composition of claim 2 wherein said 2-haloethylphosphonic acid is 2-chloroethylphosphoric acid.

6. The composition of claim 2 wherein said N-heterocyclic amide is N-methyl-2-pyrrolidone.

7. The composition of claim 2 wherein said N-heterocyclic amide is polyvinylpyrrolidone having a K value up to 90.

8. The composition of claim 2 wherein said N-heterocyclic amide is N-methyl-2-piperidone.

9. The composition of claim 2 wherein said N-heterocyclic amide is 2-pyrrolidone.

10. The composition of claim 3 wherein said mole ratio of said N-heterocyclic amide to 2-haloethylphosphonic acid is between about 0.1:1 and about 4:1.

11. The process of promoting ethylene generation of a 2-haloethylphosphonic acid of claim 1 by contacting a plant, plant part or plant situs with an ethylene generating and promoting amount of the N-heterocyclic amide of claim 1 and said 2-haloethylphosphonic acid.

12. The process of claim 11 wherein said N-heterocyclic amide and said 2-haloethylphosphonic acid are admixed with an inert carrier to form a plant growth regulant/carrier composition.

13. The process of claim 12 wherein said composition is an aqueous solution.

14. The process of claim 12 wherein said composition is a dry particulate solid.

15. The process of claim 12 wherein the concentration of said N-heterocyclic amide and 2-haloethylphosphonic acid in said composition is between about 0.1 ppm and about 45,000 ppm.

16. The process of claim 12 wherein a fruit bearing plant, plant part or plant situs is contacted with a fruit ripening amount of said composition.

17. The process of claim 12 wherein a plant, plant part or plant situs is contacted with a plant maturing amount of said composition to provide a plant maturation effect.

18. The process of claim 17 wherein an aqueous solution of said composition is applied to a cotton plant after boll set in an amount sufficient to hasten dehiscence.

19. A plant growth regulating composition of claim 1 of
   (a) a plant growth promotional amount of 2-chloroethylphosphonic acid and
   (b) N-methylpyrrolidone in an amount effective to promote the ethylene generation and promotion of said acid.

* * * * *